United States Patent
Frix et al.

(10) Patent No.: US 9,339,236 B2
(45) Date of Patent: May 17, 2016

(54) CONTINUOUS TRANSDERMAL MONITORING SYSTEM AND METHOD

(71) Applicants: James Tyler Frix, Calhoun, GA (US); Andrew Johnson, Athens, GA (US); James Mitchell Frix, Calhoun, GA (US); Robert Andrew Taylor, Anderson, SC (US)

(72) Inventors: James Tyler Frix, Calhoun, GA (US); Andrew Johnson, Athens, GA (US); James Mitchell Frix, Calhoun, GA (US); Robert Andrew Taylor, Anderson, SC (US)

(*) Notice: Subject to any disclaimer, the term of this patent is extended or adjusted under 35 U.S.C. 154(b) by 0 days.

(21) Appl. No.: 14/564,485

(22) Filed: Dec. 9, 2014

(65) Prior Publication Data
US 2015/0094551 A1    Apr. 2, 2015

Related U.S. Application Data

(63) Continuation-in-part of application No. 14/324,963, filed on Jul. 7, 2014, now Pat. No. 9,107,644.

(60) Provisional application No. 61/979,570, filed on Apr. 15, 2014, provisional application No. 61/843,111, filed on Jul. 5, 2013.

(51) Int. Cl.
*A61B 5/1455* (2006.01)
*A61B 5/00* (2006.01)
(Continued)

(52) U.S. Cl.
CPC ............... *A61B 5/721* (2013.01); *A61B 5/0205* (2013.01); *A61B 5/1121* (2013.01); *A61B 5/14551* (2013.01); *A61B 5/681* (2013.01); *A61B 5/6824* (2013.01); *A61B 5/0022* (2013.01); *A61B 5/0024* (2013.01); *A61B 5/01* (2013.01); *A61B 5/021* (2013.01); *A61B 5/02433* (2013.01); *A61B 5/0537* (2013.01); *A61B 5/067* (2013.01); *A61B 5/1112* (2013.01); *A61B 5/1118* (2013.01); *A61B 5/1126* (2013.01); *A61B 5/14517* (2013.01);
(Continued)

(58) Field of Classification Search
CPC ........... A61B 5/14552; A61B 5/14551; A61B 5/1455; A61B 5/7221; A61B 5/721; A61B 5/7214
See application file for complete search history.

(56) References Cited

U.S. PATENT DOCUMENTS 5,025,791 A * 6/1991 Niwa ............................ 600/324
6,526,300 B1 * 2/2003 Kiani et al. .................... 600/322
(Continued)

FOREIGN PATENT DOCUMENTS

DE    102006017970 A1    10/2007
WO    2006079862 A2    8/2006

*Primary Examiner* — Eric Winakur
(74) *Attorney, Agent, or Firm* — Smith Tempel Blaha LLC; Matthew T. Hoots

(57) ABSTRACT

Various embodiments of methods and systems for continuous transdermal monitoring ("CTM") are disclosed. One exemplary embodiment of a continuous transdermal monitoring system comprises a sensor package. The sensor package may include a pulse oximetry sensor having a plurality of light detectors arranged as an array. One exemplary method for continuous transdermal monitoring begins by positioning a pulse oximetry sensor system, similar to the system described immediately above, adjacent to a target tissue segment. Then, the method continues by detecting a light reflected by the target tissue segment. Then, the method continues by transmitting a pulse oximetry reading(s), based at least in part on the light reflected by the target tissue segment, of the target tissue segment. Then, the method continues by analyzing the pulse oximetry reading(s). Then, the method continues by assessing the accuracy of the pulse oximetry reading from the first light detector relative to the pulse oximetry reading from the second light detector.

15 Claims, 21 Drawing Sheets

(51) Int. Cl.

| | | |
|---|---|---|
| *A61B 5/0205* | (2006.01) | |
| *A61B 5/024* | (2006.01) | |
| *A61B 5/01* | (2006.01) | |
| *A61B 5/021* | (2006.01) | |
| *A61B 5/053* | (2006.01) | |
| *A61B 5/11* | (2006.01) | |
| *A61B 5/06* | (2006.01) | |
| *A61B 5/145* | (2006.01) | |

(52) U.S. Cl.
 CPC ............... *A61B 5/489* (2013.01); *A61B 5/684* (2013.01); *A61B 5/6831* (2013.01); *A61B 5/7221* (2013.01); *A61B 2560/0242* (2013.01); *A61B 2562/0219* (2013.01)

(56) References Cited

U.S. PATENT DOCUMENTS

| | | | |
|---|---|---|---|
| 6,801,799 B2 * | 10/2004 | Mendelson | 600/330 |
| 6,879,850 B2 * | 4/2005 | Kimball | 600/336 |
| 7,658,716 B2 | 2/2010 | Banet et al. | |
| 8,172,722 B2 | 5/2012 | Molyneux et al. | |
| 8,253,586 B1 | 8/2012 | Matak | |
| 8,289,185 B2 | 10/2012 | Alonso | |
| 8,396,687 B2 | 3/2013 | Vock et al. | |
| 8,477,046 B2 | 7/2013 | Alonso | |
| 2008/0146895 A1 | 6/2008 | Olson et al. | |
| 2009/0227852 A1 | 9/2009 | Glaser | |
| 2009/0326347 A1 * | 12/2009 | Scharf | 600/323 |
| 2010/0298683 A1 | 11/2010 | Cabrera et al. | |
| 2011/0112379 A1 * | 5/2011 | Li et al. | 600/300 |
| 2011/0166491 A1 | 7/2011 | Sankai | |
| 2012/0172679 A1 | 7/2012 | Logan et al. | |
| 2012/0221254 A1 | 8/2012 | Kateraas et al. | |
| 2013/0125295 A1 | 5/2013 | Krueger | |
| 2013/0321168 A1 | 12/2013 | Mahony et al. | |
| 2014/0000011 A1 | 1/2014 | Johnson | |

\* cited by examiner

SUPERCIFICIAL VIEW
DEEP VIEW
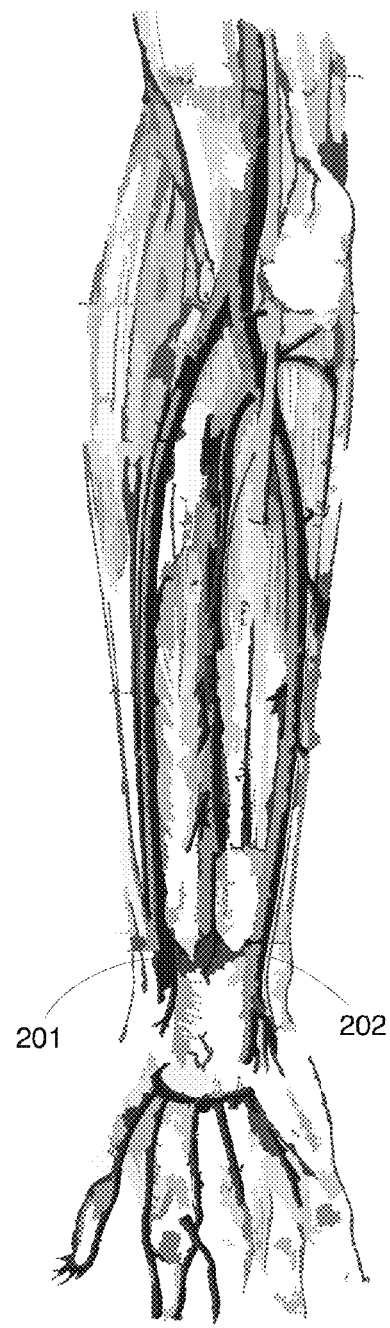
FIG.1
FIG. 2

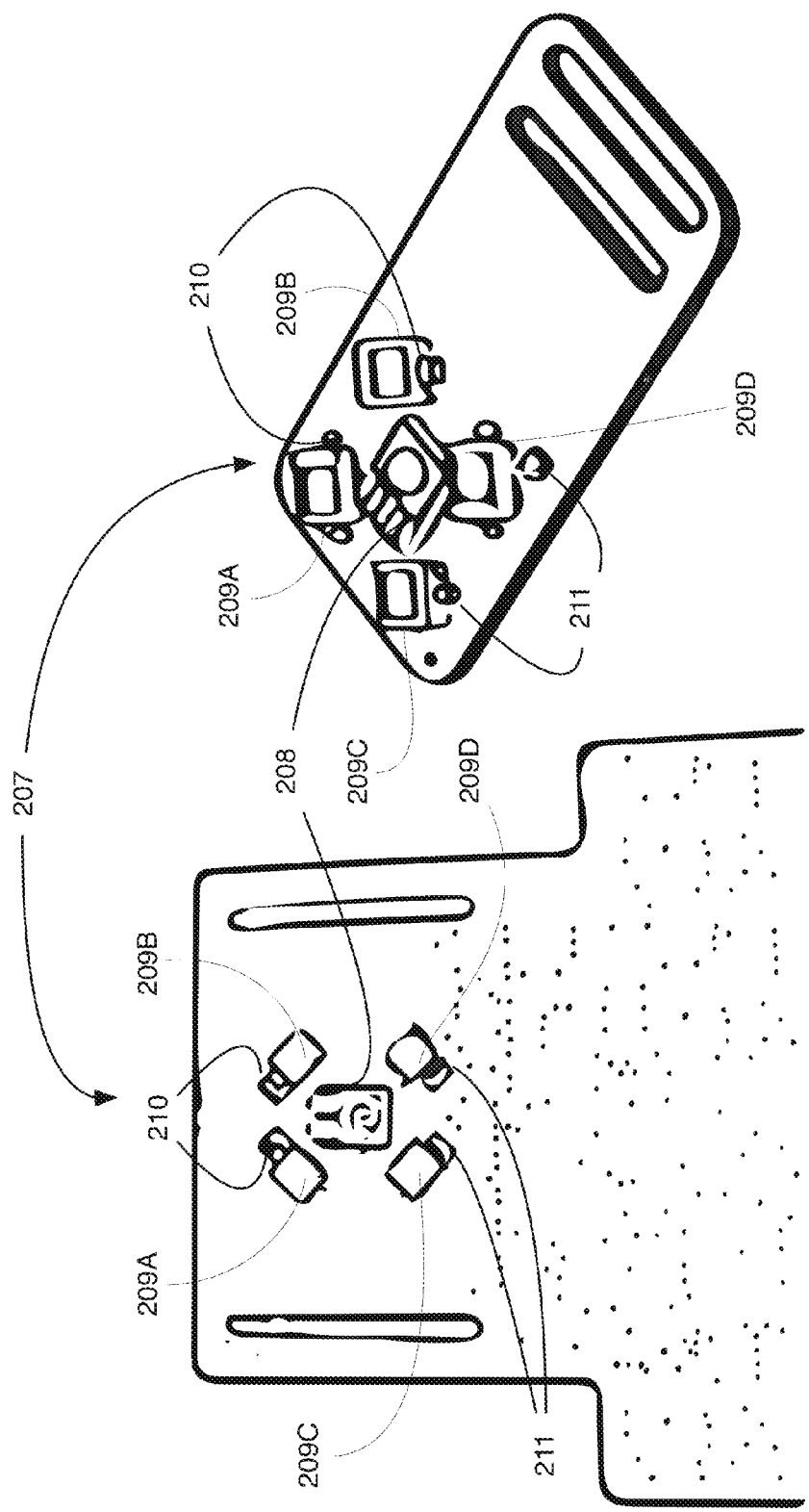

CONTINUOUS TRANSDERMAL MONITORING SYSTEM AND METHOD

CROSS-REFERENCE TO RELATED APPLICATIONS

This U.S. non-provisional utility patent application is a continuation-in-part of, and claims priority under 35 U.S.C. §120 to, the U.S. non-provisional utility patent application entitled "CONTINUOUS TRANSDERMAL MONITORING SYSTEM AND METHOD," filed on Jul. 7, 2014 and assigned application Ser. No. 14/324,963, which claims priority under 35 U.S.C. §119(e) to, and incorporates by reference the entire contents of, U.S. provisional patent application entitled "CONTINUOUS TRANSDERMAL MONITORING SYSTEM" filed on Jul. 5, 2013 and assigned application Ser. No. 61/843,111, and U.S. provisional application entitled "CONTINUOUS TRANSDERMAL MONITORING SYSTEM" filed on Apr. 15, 2014 and assigned application Ser. No. 61/979,570. The entire contents of application Ser. No. 14/324,963, application 61/843,111 and 61/979,570 are hereby incorporated by reference.

BACKGROUND

Pulse oximetry is a technique known in the art for measuring absorbencies in pulsing arterial blood. As one of ordinary skill in the art of pulse oximetry understands, a pulse oximeter may also be used to monitor real time heart rate and arterial oxygen saturation levels.

Pulse oximetry works on the basic concept of light absorption by hemoglobin, the oxygen carrying molecule in red blood cells. Hemoglobin has four oxygen binding sites per molecule. The molecule may absorb a certain amount of light emitted by a pulse oximeter, based on how many of the molecule's oxygen binding sites are bound to an oxygen molecule. The wavelength of unabsorbed light sensed by the pulse oximeter may be used to calculate the amount of oxygen bound per hemoglobin molecule. By taking an overall average of these sites, the percentage of the total blood oxygen saturation is calculated.

To accurately monitor light absorption, certain pulse oximeters must be placed on the body in an area where the skin is thin enough for light to pass through yet has enough vascular tissue to generate an acceptable measurement (e.g., ear lobe or tip of an index finger). Certain other pulse oximeters, however, monitor light absorption by measuring the amount of light reflected from a user's body, as opposed to the amount of light that passes through. Reflective pulse oximeters leverage the fact that hemoglobin molecules reflect certain wavelengths of light based on the number of oxygen-binding sites that are bound to oxygen and, as such, may be placed on the body in areas that have dense capillary beds and/or arteries near the skin surface (e.g., underside of the wrist, chest sternum, forehead, etc.).

Notably, pulse oximetry measurements, whether taken with a "pass-through" pulse oximeter or a "reflective" pulse oximeter, are prone to inaccuracies due to electrical noise introduced by user movement. The effect of motion artifact on the accuracy of a pulse oximetry measurement makes pulse oximetry technology known in the art less than ideal for real time pulse oximetry monitoring in users that are moving, such as athletes, runners, etc. Body movement during a reading may provide inaccurate, misleading, or ineffective data. Therefore, there is a need in the art for a system and method that provides an accurate pulse oximetry reading, as well as other physiological calculations and/or combinations of physiological calculations, when a user is in motion.

SUMMARY OF THE DISCLOSURE

The presently disclosed embodiments, as well as features and aspects thereof, are directed towards a system and method for continuous transdermal monitoring that may include measuring pulse oximetry of a subject. The pulse oximetry measurement may be intermittent or it may be by constant measurement. In some embodiments, the method may include measuring the pulse of the subject at a moment during a time interval t, measuring the subject's acceleration at about the moment, and determining whether the pulse measured at the moment is at or about a minimized moment of subject acceleration and/or deceleration.

In an exemplary embodiment, the present disclosure includes a system and method for measuring pulse oximetry of a subject by interval measurement which includes measuring an acceleration or deceleration of a body part of a subject, determining whether the acceleration or deceleration is within a minimum range, and signaling a pulse oximeter to take a pulse oximetry reading.

One exemplary method for continuous transdermal monitoring begins by monitoring an output signal from an accelerometer. The accelerometer output signal may indicate acceleration and deceleration of a body part of a user, such as the user's wrist. Based on the accelerometer output signal, it may be determined that the body part of the user has decelerated to a minimum, e.g., substantially zero. With a determination that the body part has decelerated to substantially zero, or has not accelerated beyond substantially zero, the method may determine a reading from a pulse oximeter associated with the accelerometer. Advantageously, the pulse oximetry reading, or a reading from other sensors associated with the accelerometer, may be optimally accurate as motion artifact may be minimized. The pulse oximetry reading may be recorded for later query and/or rendered for the benefit of the user.

One exemplary embodiment of a continuous transdermal monitoring system comprises a sensor package. The sensor package may include a pulse oximetry sensor having a plurality of light detectors arranged as an array. The plurality of light detectors having a first light detector and a second light detector and possibly various other light detectors. Regardless of the number of light detectors, the light detectors are each, respectively, configured to detect a light reflected by the target tissue segment and transmit a pulse oximetry reading of the target tissue segment. It is envisioned that the pulse oximetry reading is based, at least in part, on the light reflected by the target tissue segment. The sensor package is configured to analyze the pulse oximetry reading from the plurality of light detectors and assess the relative accuracy of the pulse oximetry reading from the plurality of light detectors.

One exemplary method for continuous transdermal monitoring begins by positioning a pulse oximetry sensor system, similar to the system described immediately above, adjacent to a target tissue segment. Then, the method continues by detecting a light reflected by the target tissue segment. Then, the method continues by transmitting a pulse oximetry reading(s), based at least in part on the light reflected by the target tissue segment, of the target tissue segment. Then, the method continues by analyzing the pulse oximetry reading(s). Then, the method continues by assessing the accuracy of the pulse oximetry reading from the first light detector relative to the pulse oximetry reading from the second light detector.

BRIEF DESCRIPTION OF THE DRAWINGS

In the drawings, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral encompass all parts having the same reference numeral in all figures.

FIG. 1 is an illustration of the anatomy of a user's right arm showing major arteries depicted from a superficial view (anatomy under the dermis and epidermis);

FIG. 2 is an illustration of the anatomy of a user's right arm showing major arteries depicted from a deep view (anatomy under the dermis, epidermis and partial muscle lawyer);

FIG. 8 is a schematic illustration of a non-limiting embodiment of the continuous transdermal monitoring ("CTM") circuit board of FIG. 7, shown from the side of the circuit board that is proximate to the user's arm;

FIG. 9 is a top and side perspective view, respectively, of a non-limiting embodiment of the continuous transdermal monitoring ("CTM") circuit board of FIG. 7, shown from the side of the circuit board that is proximate to the user's arm;

DETAILED DESCRIPTION

Figure 3:
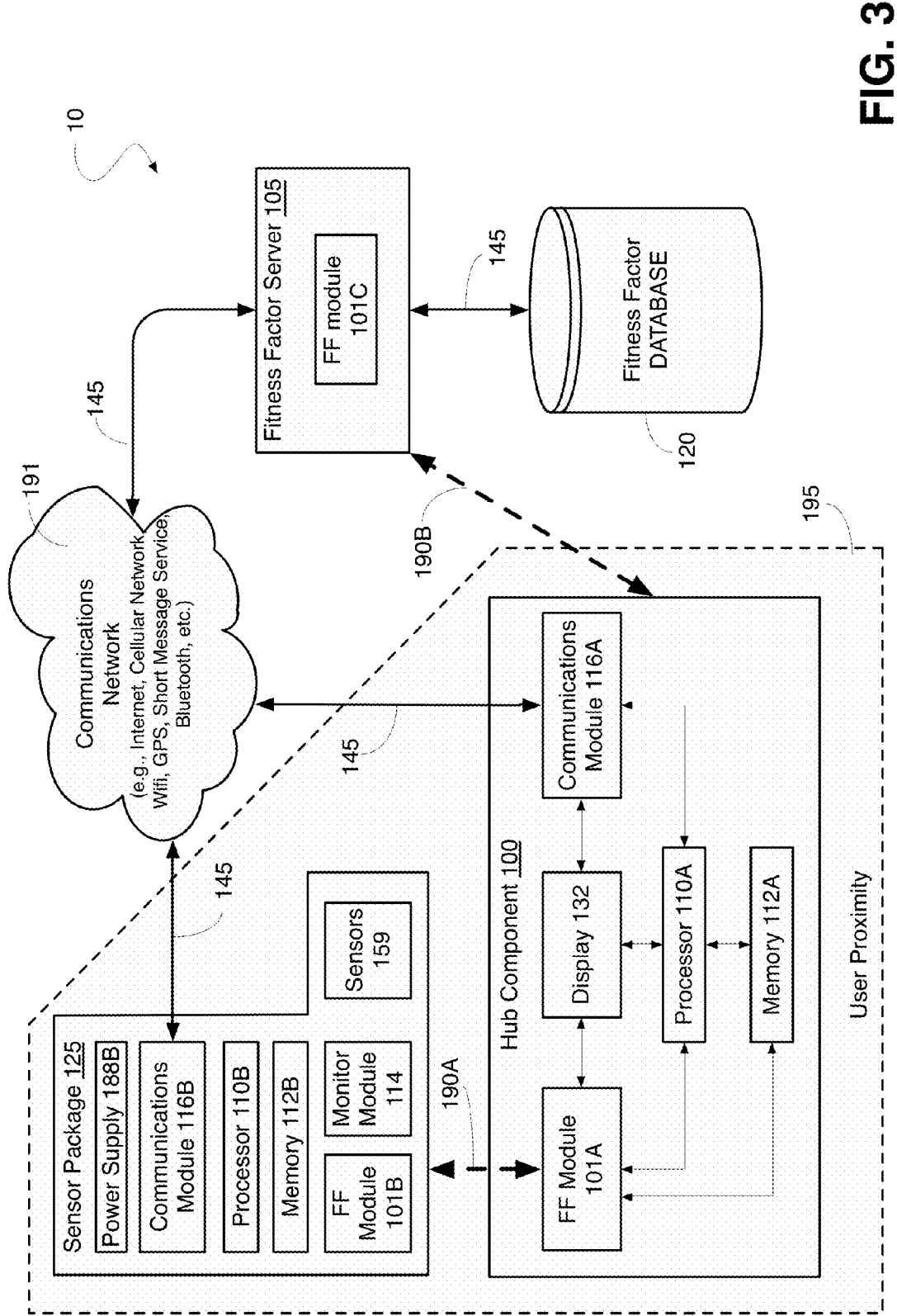
FIG. 3 is a high level functional block diagram illustrating an exemplary architecture of a system for continuous transdermal monitoring ("CTM")

Aspects, features and advantages of several exemplary embodiments of continuous transdermal monitoring ("CTM") systems and methods will become better understood with regard to the following description in connection with the accompanying drawing(s). It will be apparent to one of ordinary skill in the art that the described CTM embodiments provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, any use of absolute terms such as, for example, "will," "will not," "shall," "shall not," "must" and "must not" are not meant to limit the scope of the disclosure as the particular CTM embodiments disclosed herein are merely exemplary.

The word "exemplary" is used herein to mean serving as an example, instance, or illustration. Any aspect described herein as "exemplary" is not necessarily to be construed as exclusive, preferred or advantageous over other aspects.

The term "motion artifact" is used herein to represent all errors, caused by unaccounted-for motion, in the measurement taken by an analytical reader, e.g., a pulse oximeter. An analytical measurement will contain a motion artifact for a variety of reasons, e.g., the displacement of the target tissue segment relative to the pulse oximeter and/or the displacement of the pulse oximeter relative to the target tissue segment during the reading. Therefore, a motion artifact will cause the analytical measurement to be inaccurate and/or imprecise. One having ordinary skill in the art understands that a motion artifact is also related to a displacement in the relative orientation of the components of an analytical reader.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

As used in this description, the terms "component," "database," "module," "system," and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component.

One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet with other systems by way of the signal).

In this description, the terms "central processing unit ("CPU")," "digital signal processor ("DSP")," "graphical processing unit ("GPU")," "processing component" and "chip" are used interchangeably. Moreover, a CPU, DSP, GPU or chip may be comprised of one or more distinct processing components generally referred to as "core(s)."

In this description, the term "portable computing device" ("PCD") is used to describe any device operating on a limited capacity power supply, such as a battery. Although battery operated PCDs have been in use for decades, technological advances in rechargeable batteries coupled with the advent of third generation ("3G") and fourth generation ("4G") wireless technology have enabled numerous PCDs with multiple capabilities. Therefore, a PCD may be a cellular telephone, a satellite telephone, a pager, a PDA, a smartphone, a navigation device, a smartbook or reader, a media player, a combination of the aforementioned devices, a laptop computer with a wireless connection, a remote sensor package worn by a user, among others.

Continuous transdermal monitoring ("CTM") embodiments, as well as features and aspects thereof, are directed towards providing a system and method for measuring pulse oximetry of a subject by constant measurement which may include measuring the pulse of the subject at a moment during a time interval t, measuring the subject's acceleration at about the moment, and determining whether the pulse measured at the moment is at or about a minimized moment of subject acceleration. Certain CTM embodiments may also monitor via one or more sensors any number of physiological and/or non-physiological parameters associated with the subject including, but not limited to, pulse rate, blood oxygen saturation, transdermal core temperature, Global Positioning System ("GPS") coordinates, 3-axis accelerometer outputs, skin and ambient temperature readings, hydration levels, and barometric readings.

Certain CTM embodiments may include a pulse-oximeter in a sensor package that utilizes reflective, light-absorption technology. The pulse oximeter sensor may be configured to transmit light at two different wavelengths, such as for example 660 nm and 940 nm, through the skin and into an artery of a user. As one of ordinary skill in the art would understand, some of the transmitted light may be reflected and, based on the amount of light reflected and sensed by the pulse oximeter sensor, used to calculate pulse rate and arterial blood oxygen saturation.

The sensor package of a CTM embodiment may be placed on the wrist and worn like a wristwatch. Other CTM embodiments may include a sensor package that is integrated into sports equipment such as wristbands, sweatbands, braces, shoulder pads, helmets, mouthpieces, etc. By having a durable encasement and a monitoring system that accounts for movement, the circuitry within the sensor package, and the integrity of the data it generates, may be protected from impact and movement.

It is envisioned that a sensor package of a CTM embodiment may be placed on the body of a user over any artery or arterial bed, such as the forehead, ear, bicep, ankle, etc. As such, the particular location of a sensor package, as applied to a user, will not limit the scope of a CTM embodiment. For example, in a football application, the sensor package may be implanted into the front of a player's helmet and targeted at the forehead, or integrated into the player's shoulder pads right over the sternum. Both the forehead and the sternum offer superficial arterial beds that may present an opportunity to yield good accuracy in reflective pulse oximetry measurement, as would be understood by one of ordinary skill in the art of pulse oximetry.

As another example, in an application for use by a patient in a hospital, it is envisioned that the sensor package of a CTM embodiment may be worn on the wrist or ankle for ease of use. During trauma events, when the blood flow to capillary and arterial beds is restricted and motion artifact is introduced from the patient's constant movement and writhing in pain, the sensor package of the CTM embodiment may obtain useful measurements while worn on the arm, leg or trunk of the body.

A CTM embodiment may include components in addition to a pulse oximeter to track a user's motion and surrounding environment. For example, it is envisioned that a CTM embodiment may include a GPS sensor and accelerometer for monitoring movement, distance, velocity, and acceleration of the user. It is also envisioned that a CTM embodiment may include a displacement sensor and/or accelerometer for monitoring movement, distance, velocity, and acceleration of the pulse oximetry sensor relative to the user. Moreover, some embodiments may include combinations of a barometer, skin and ambient temperature probe, core temperature sensor, and a hydration sensor for monitoring a user's elevation during a workout, ambient temperature exposure, skin temperature and sweat-fluid composition along with the athlete's core body temperature. Certain embodiments may also include an ultraviolet ("UV") sensor for monitoring the user's sun exposure and or an infrared sensor for visualizing a blood vessel within a target tissue segment on a user. Using one or more readings generated by the sensors, a CTM user's blood pressure may be estimated using linear regression. The accelerometer may also be used to determine the amount of time the user sleeps by tracking movement. Any or all of these readings may be taken in real time and relayed wirelessly to a portable computing device, or other computing device, such as a Smartphone or computer.

Certain CTM embodiments may include an integrated light emitting diode ("LED") screen which may render continuous information to the user of the CTM embodiment. A CTM embodiment may be equipped with programmable alarms that may sound if any reading recognized by the sensor package falls outside of a desired, preset range. Notably, it is envisioned that certain CTM embodiments may leverage a single computing device, or "hub" device, in communication with two or more sensor packages, thereby providing for a single user to monitor several other users, each associated with a sensor package.

It is envisioned that some CTM embodiments may include a hub device, such as a portable computing device that is communicatively linked to one or more sensor packages using Bluetooth or another short wave radio signal. Certain CTM embodiments may store data collected by a sensor package, output data to a user in real time, transmit collected data to a remote device such as a server, or any combination thereof. The collected data may be leveraged by certain CTM embodiments to generate a general fitness factor from a weighted computation of multiple sensor outputs. It is envisioned that the fitness factor output may be generated by algorithms that are customized by the user such that certain data inputs are weighted according to user selection.

In exemplary CTM embodiments, the fitness factor may be calculated from an algorithm based on data gathered from one or more studies that quantify various heart rate levels during and after exercise. A user's core temperature reading taken in correlation with the heart rate readings, along with other physiological readings from a sensor package such as blood pressure and oxygen saturation, may contribute to calculation of a fitness factor according to a fitness factor algorithm in a CTM embodiment. Moreover, individual metrics such a metabolic expenditure, resting heart rate, maximum heart rate, gender, age, heart rate variability, heart rate recovery, height, weight, and other metrics may also be tracked and incorporated into the fitness factor in some embodiments.

As described above, it is envisioned that a fitness factor may be calculated based on a statistically verified weighted scoring system composed of the various health metrics input by a user and/or monitored and tracked by a sensor package/hub device. The software package may generate data that may inform a care-giver or patient or athlete about a general fitness level, thus allowing a user to smartly customize activities. For instance, a football team using a CTM embodiment may determine how demanding practice should be for a given week based on the players' average fitness level according to outputs generated by a fitness factor algorithm. Similarly, a fitness factor algorithm according to a CTM embodiment may provide an individual user with a unitless output against which to measure improvement of a general physical fitness level.

A CTM embodiment may feature onboard memory storage as well as a wireless transmitter in order to store and/or send real time output data. The antenna for the wireless transmitter and the printed circuit board may be flexible and embedded along the curvature of a component of the CTM embodiment, such as a sensor package. As previously described, a sensor package component of a CTM embodiment may include any number of onboard sensors including, but not limited to, a 3-axis or 6-axis accelerometer, GPS receiver, barometer, ambient and skin temperature gauges, hydration sensor, core body temperature sensor, displacement sensor, infrared sensor and a reflective pulse-oximeter. Notably, any combination of the sensors may reside within a sensor package and/or a hub device of a CTM embodiment.

Certain CTM embodiments may include algorithms for collecting accurate pulse oximetry readings, as well as other sensor readings, by minimizing the effects of motion artifact errors when the reading(s) is taken. An exemplary algorithm involves measuring when user motion and/or movement is at a minimum. Based on a preset input defining what constitutes minimum movement, readings from an accelerometer and/or other methods of position measurement may be used to recognize when user movement is at a minimum. Consequently, a CTM embodiment may recognize readings taken from other sensors at a point in time that is close to the time of minimal user movement as being accurate. In such an embodiment, for example, an accelerometer in a sensor package may be effectively functioning as the on/off control for the oximeter sensor, i.e. the accelerometer output may trigger the pulse oximeter sensor to take a reading when user movement is at a minimum, and vice versa.

Another exemplary algorithm involves measuring when user motion and/or movement causes the pulse oximetry sensor to shift position while worn by the user. A preset input defining what constitutes a shift in position, readings from an accelerometer and/or other methods of inferring a shift in position may be used to recognize when the pulse oximetry sensor shifted position. Consequently, a CTM embodiment may recognize readings taken from other sensors at a point in time that is close to the time when the pulse oximetry sensor shifted position. In another embodiment, for example, the output of an accelerometer may be effectively leveraged to assess the relative accuracy of a pulse oximetry reading.

A pulse oximeter included in a sensor package component of a CTM embodiment may comprise a red LED that may be pulsed for approximately 50 microseconds then turned off. Subsequently, after 450 more microseconds an infrared LED may be pulsed for approximately 50 microseconds then turned off. After 450 more microseconds, the red LED may be turned back on and the cycle may repeat. The duration of the pulse oximeter cycle may be programmable and therefore subject to change in some CTM embodiments. Once the light generated by the LEDs is reflected off of an artery or artery bed of a user, it may be absorbed by a light detector which may emit a small current of a few micro amps, as would be understood by one of ordinary skill in the art. A photodiode is an example of a light detector; however, a person having ordinary skill in the art recognizes various other embodiments of light detectors including a composite photodiode sensor. It is envisioned that any array of multiple photodiodes may be employed to obtain a plurality of independent pulse oximetry readings for differently defined target tissue segments. It is possible that these defined target tissue segments may overlap; the pulse oximetry readings for differently defined target tissue segments is likely to be different as would be understood by one of ordinary skill in the art.

In the exemplary embodiment, the current from any light detector in an array of light detectors may be sent to a transimpedance amplifier, sometimes referred to as an op-amp, which may convert the few micro-amps of current into a few millivolts, as is understood by one of ordinary skill in the art of electronics. The signal may then be sent to a bandpass pass filter that may filter out all the noise above 5 Hz and below 0.5 Hz, for example. It is envisioned that this may allow a pulse rate resolution of as low as 20-30 beats per minute and as high as 300 beats per minute in some CTM embodiments. It is further envisioned that a bandpass filter width may be adjusted or modified to achieve different resolutions. From there, the voltage may be passed through a gain amplifier. The gain amplifier may set a gain and DC offset in order to properly set the voltage's output signal level equal to the microcontroller's ADC range, as would be understood by one of ordinary skill in the art of electronics. Once that is accomplished, it may be sent through an analog to digital converter ("ADC") and into a microcontroller for further processing and output.

As described above, a sensor package component in a CTM embodiment may include a hydration sensor, reflective pulse co-oximeter, and/or a core body temperature sensor. The hydration sensor may be comprised of two electrodes with a potentiometer attached. Based on the amount of current conducted between the electrodes, the electrolyte concentration in the user's sweat may be calculated, as would be understood by one of ordinary skill in the art. This data may be used by a CTM embodiment to determine the user's overall hydration and electrolyte levels. If a single electrolyte needs to be targeted, such as sodium for example, it is envisioned that an electrolyte specific electrode may be used, such as a sodium selective ion electrode.

A pulse co-oximeter included in a CTM embodiment may function in almost the same way as the reflective pulse oximeter described above. A pulse co-oximeter differs from a reflective oximeter, however, in that the co-oximeter may send several different wavelengths of light through a blood vessel in a target tissue segment in order to distinguish oxyhemoglobin from carboxyhemaglobin, as would be understood by one of ordinary skill in the art. As such, a CTM embodiment that includes a co-oximeter in the sensor package may provide for the calculation of a user's total hemoglobin count. Notably, a hemoglobin count may be of utmost importance in field, clinical and surgical settings as it may set off an early warning to massive bleeding or other trauma events.

A core body temperature sensor included in the sensor package of a CTM embodiment may also leverage reflective technology. Water absorption rates in the near infrared spectrum are sensitive to temperature changes. As temperature increases, water's absorption, over these near infrared wavelengths, undergoes a blue-shift and narrows while increasing in intensity. By tracking these shifts and intensity increases with diffuse optical spectroscopy, a CTM embodiment may calculate a spectral arterial temperature representative of a user's core body temperature.

Physiological and non-physiological data monitored, tracked and collected by a sensor package of a CTM embodiment may be transmitted to a hub device if present, such as a portable computing device in the form of a Smartphone with an associated CTM application or a remoted server with associated software. The hub device may receive the data via a wireless transmission and then sort it into an array that compartmentalizes the data based upon the source of the data, i.e the GPS transceiver, accelerometer, barometer, etc. Next, the data may be processed by a CTM algorithm that calculates any one or more of the arterial oxygen saturation, instantaneous velocity, distance traveled, G-force, ambient and skin temperature, heart rate, acceleration, core temperature, blood pressure, and/or general fitness level of a user. Notably, it is envisioned that the collected data and/or outputs generated by the collected data may be rendered to a user according to a preferred format.

The one or more integrated circuits and components of a given CTM embodiment may be protected with a hard plastic covering. It is envisioned that an outer band housing all, or a portion of, a sensor package may be worn by a user and may also be made of a protective material such as neoprene, flexible plastic, rubber, or some other type of flexible and protective fabric. One or more components in a CTM embodiment may feature a strap or some other means to tighten the embodiment down in order to prevent and/or limit movement or slippage relative to a user's person. It is envisioned, however, that for purposes of comfort, a CTM embodiment has aspects, features and functions that allow the CTM to compensate for motion noise when the CTM unavoidably shifts position relative to a user's person.

Any component of a CTM embodiment may also be made elastic or form fitting to possibly eliminate the strap. For instances when one or more components of a CTM embodiment is integrated into sports equipment, it is envisioned that the electronics may be protected by that equipment. A helmet may have the device imbedded into the padding over the forehead, and a wrist or ankle brace/guard may have the device sewn into the fabric and protected by the brace or guard itself, for example. A mouthpiece may be designed with the device molded into it, as could an earpiece perhaps used for communication between teammates. Integration into any and all possible sports equipment is envisioned.

Exemplary CTM embodiments, as well as features and aspects thereof, are directed towards providing a system and method for measuring pulse oximetry of a subject by constant measurement which includes measuring the pulse of the subject at a moment during a time interval t, measuring the subject's acceleration at about the moment, and determining whether the pulse measured at the moment is at or about a minimized moment of subject acceleration.

In an exemplary embodiment, a CTM algorithm begins at beginning time t. A pulse oximeter may be attached to the subject at a convenient point of its body and the pulse oximeter may take readings at either predefined intervals or, in another embodiment, intervals dependent on the movement of the subject.

An accelerometer attached to the patient or user, which accelerometer is proximate to the pulse oximeter, may take readings at or about the same moment the pulse oximeter takes readings. The term "at or about the same" may mean substantially simultaneous, or from about 1 to about 10 milliseconds, or from about 1 to about 5 milliseconds, or from about 1 to about 3 milliseconds, depending on the particular CTM embodiment. The readings of the pulse oximeter and the accelerometer are correlated by the moments of reading over time interval t.

The moments of minimized acceleration are selected and the correlated pulse oximetry readings are selected. The selected moments of pulse oximetry are then used to determine the oxygen levels of the subject during time interval t and those oxygen levels are used for further evaluation of the subject. Advantageously, by using those pulse oximetry readings which are correlated to moments of minimized acceleration, CTM embodiments may effectively mitigate error in the pulse oximetry readings that would be otherwise introduced from motion artifact.

An exemplary system and method for measuring pulse oximetry of a subject by measurement at minimized movement points includes measuring an acceleration of a subject, determining whether the acceleration is within a minimum range, and signaling a pulse oximeter to take a subject pulse oximetry reading if the acceleration is within the minimum range.

In an exemplary embodiment, a pulse oximeter may be attached to the subject at a convenient point of its body. An accelerometer attached to the patient, which accelerometer is proximate and in communication with the pulse oximeter, make take readings. The accelerometer reading may be compared to a predefined set of minimized accelerometer readings. If the accelerometer falls within the range, then the accelerometer signals the pulse oximeter to take a reading, and the reading may be transmitted to a data storage module or software module.

In another exemplary embodiment, the accelerometer reading and the pulse oximetry reading are substantially correlated such that they are read at substantially simultaneous points in time, or from about 2 to about 20 milliseconds, or from about 2 to about 10 milliseconds, or from about 1 to about 3 milliseconds, depending on CTM embodiment.

In certain CTM embodiments, it is envisioned that pulse oximetry readings may be taken from the underside of the wrist which offers superficial vasculature from the radial and ulnar artery. In these embodiments, it is envisioned that more accurate pulse oximetry measurements may be taken during tachycardia, e.g., at high pulse rates (for example, at pulse rates at or greater than about 100 beats per minute to about 250 beats per minute), as compared to other sites. In another embodiment, the accelerometer and/or the pulse oximeter may be positioned on or about the top side of the wrist when during brachicardia, e.g., at low pulse rates (for example at pulse rates at or lower than 60 beats per minute), more accurate readings may be attainable.

In certain CTM embodiments, the CTM is structured and configured to obtain pulse oximetry readings from the major arteries (as opposed to superficially located capillary beds) of a target tissue segment of user. Other embodiments may be structured and configured to obtain pulse co-oximetry readings from the major veins. Other embodiments may be structured and configured to obtain pulse oximetry and co-oximetry readings from any specific blood vessel of the target tissue segment. It is envisioned that a CTM embodiment may comprise a pulse oximetry sensor specifically configured to target a tissue segment wherein sufficient translucent tissue exists between the pulse oximetry sensor and the blood vessel within the target tissue segment. It is also envisioned that the pulse oximetry sensor may be configured to provide accurate and precise measurements even when the user is moving and causing a physical shift in the pulse oximetry sensor location relative to the target tissue segment.

It is envisioned that a pulse oximetry sensor configured to provide accurate and precise measurements when the user is moving may comprise a light emitter, a plurality of light detectors arranged in a particular formation or array, a light detector dedicated accelerometer and a light detector dedicated displacement sensor. The plurality of light detectors may be structured and positioned to function as an array of independent light detectors and configured to obtain a plurality of independent pulse oximetry readings for differently defined target tissue segments. The light detector dedicated accelerometer may be configured to detect the acceleration associated with one or more light detectors of the plurality of light detectors. Similarly, it is envisioned that the light detector dedicated displacement sensor may be configured to measure the displacement of one or more light detectors of the plurality of light detectors from a specific target tissue segment. In at least one embodiment, the light detector dedicated displacement sensor comprises an infrared sensor configured to visualizing a blood vessel within a target tissue segment.

In one CTM method embodiment, a pulse oximetry determination is performed using an array of light detectors. First, separate pulse oximetry readings from the individual light detectors of a light detector array for a target tissue segment are received. Next, a processor may analyze the separate pulse oximetry readings from the individual light detectors in an effort to determine which of the individual light detectors is best positioned to generate a useful pulse oximetry reading, i.e. which light detector is best inline with the target tissue segment. To do this, the processor may assess the relative accuracies of the separate pulse oximetry readings with respect to the target tissue segment. For example, the processor may assess which of the readings is the highest reading and from there infer that the light detector associated with the highest reading is most likely the light detector most closely positioned to the target tissue (e.g., over a certain artery).

Then, the processor may identify a preferred pulse oximetry reading(s) from the separate pulse oximetry readings, based at least in part, on the assessed relative accuracies. Once the preferred pulse oximetry reading is identified, the processor may designate a preferred light detector(s) from the light detectors, based at least in part, on the identified preferred pulse oximetry reading(s). Subsequently, the pulse oximetry reading from the designated preferred light detectors may be output for processing, leveraging, and/or rendering for the user or any other third party and/or stored for later query.

Continuing the exemplary CTM method, further separate pulse oximetry readings from the individual light detectors of a light detector array for a target tissue segment may be received. The processor may then again analyze the newly received separate pulse oximetry readings from the individual light detectors and reassess the relative accuracies of the newly received seperate pulse oximetry readings with respect to the target tissue segment. Then, the processor may identify a preferred pulse oximetry reading(s) from the newly received seperate pulse oximetry readings, based at least in part, on the reassessed relative accuracies. If the identified preferred pulse oximetry reading(s) would lead to a change in the preferred light detector(s) from the light detectors, then the processor may redesignate a preferred light detector(s) from the light detectors, based at least in part, on the newly identified preferred pulse oximetry reading(s). Subsequently, the pulse oximetry reading from the redesignated preferred light detectors may be output for processing, leveraging, and/or rendering for the user or any other third party and/or stored for later query.

In a similar CTM embodiment to that just described, a pulse oximetry determination may be performed using an array of light detectors; however, in this embodiment, instead of identifying a preferred pulse oximetry reading(s) from the seperate pulse oximetry readings, based at least in part, on the assessed relative accuracies, the method may identify a relative weight of importance assignable to each pulse oximetry reading from the light detectors. Then, instead of designating a preferred light detector(s) from the light detectors, the exemplary CTM embodiment computes a composite pulse oximetry reading(s), based at least in part on the assigned relative weights of importance.

Then, the exemplary CTM method repeats to reassess the merit of the weighting attributed to the various readings. If the identified relative weight of importance assignable to each pulse oximetry reading from the light detectors has not changed from the previous determination, then the computed composite pulse oximetry reading(s) may be output for processing, leveraging, and/or rendering for the user or any other third party and/or stored for later query. If, however, after reassessment it is determined that the identified relative weight of importance assignable to each pulse oximetry reading from the light detectors has changed, then, the processor may recompute a composite pulse oximetry reading(s), based at least in part on reassigned relative weights of importance.

In another CTM embodiment, there may be provided a method of determining a General Fitness Factor (referred to in the present description as "GFF" or "FF") using, in whole or in part, the methods of pulse oximetry measurements described herein. The GFF may be determined using an algorithm that objectively calculates fitness based on weighted inputs of physiological and/or non-physiological inputs and quantifies the data in a single unitless number.

In an exemplary CTM embodiment that generates a fitness factor, the GFF may enable physicians, trainers, and even individuals to track fitness in a simple and effective manner. The algorithm may be customizable and may comprise inputs from a motion-tracking device, including but not limited to a global positioning system ("GPS"), an accelerometer, and gyrometer along with a continuous heart rate monitor as well as data from other sources such as a skin temperature gauge or breathing apparatus.

Utilizing these technologies, objective, unique, and specific fitness data may be captured, enabling a CTM algorithm to calculate a quantified fitness factor value using objective data associated with physiological and/or non-physiological parameters including, but not limited to, resting heart rate (HR), maximum heart rate (MHR), projected maximum heart rate (PMHR), heart rate variability (HRV), heart rate recovery (HRR), and movement profile (MP). In some embodiments, it is envisioned that the only user inputs may be age, height, and weight. It is envisioned that weighted combinations of such objective data associated with physiological and/or non-physiological parameters may be used by CTM embodiments to generate a fitness factor.

HR may mean the number of times a heart beats during a given time frame while an individual is not moving. For instance, if the heart beats 200 times over a three minute span, the HR is 67. MHR may mean the maximum heart rate reached during a time of physical activity. PMHR may mean the projected maximum heart rate for an individual based on age and is equal to (220—subject age), for example. HRV may mean the standard deviation of heart rate during a period of physical exertion. HRR may mean the time span between the end of a period of physical exertion and when heart rate returns to resting heart rate levels. MP may mean the movement during physical exertion correlated to the time taken to perform the movement.

In a certain embodiment, MP may be measured from the moment when the heart rate rises above resting levels over a short period of time, which may be between 1 and 20 seconds, and may end when the heart rate returns to a resting level. MP may take into account how long a person is in motion and how much exertion occurs during that movement (depicted by MHR). This aids in distinguishing the type of movement occurring, for example, whether the movement be a 100-yard sprint, a pull-up, or a three-mile run.

For example, a CTM algorithm used by a given CTM embodiment may calculate a weighted summation of the various inputs. Each of the analyzed inputs may be recognized by the user as not having an equal effect on determining the user's physical fitness. For instance, HRR may be considered a dominant predictor of fitness, while age may not be considered a strong indicator of fitness. In addition, some inputs may have an inverse correlation with fitness levels, such as HR, and these inputs may be weighted to reflect the negative association. As a result, each of the inputs may be assigned a contributory weight to the final quantitative number. The total contribution may then be divided by a constant to get the final Fitness Factor to fall on a certain scale such as from 1 to 10 or even 1 to 1000, for example.

For example, a fitness factor calculation, adjusted by a constant to fit on a scale of 1 to 100 may be generated from an exemplary CTM algorithm in the following manner:

|  | Data | Weight | Contribution |
| --- | --- | --- | --- |
| Age | 24 | 1 | 24 |
| Height (inches) | 60 | 0.5 | 30 |
| Weight (pounds) | 110 | 0.363636364 | 327.2727273 |
| Resting HR | 50 | 4 | 200 |
| Predicted Maximum HR | 186 | 1 | 186 |
| Maximum HR during workout | 160 | 1 | 160 |

-continued

|  | Data | Weight | Contribution |
| --- | --- | --- | --- |
| HR Recovery (seconds) | 500 | 0.02 | 200 |
| Heart Rate Variability (HRV) | 10 | 10 | 10 |
| Movement Profile (MP) | 120 | 1 | 120 |
| Total |  |  | 1257.272727 |
| Fitness Factor |  |  | 62.86363636 |

Moreover, the algorithm may continue to adapt to the subject and learn its movement habits to better tailor a movement profile. The algorithm may further comprise a kernel consisting of a moving average over a given time frame. In addition, the calculation may be adjusted to fit a certain scale, such as from 1 to 10 or even 1 to 1000.

An exemplary CTM embodiment running an algorithm for generating a fitness factor of a subject, with age, height, weight, and resting heart rate known, begins at a certain time. For a time i, the exemplary algorithm measures pulse oximetry from the beginning of physical exertion to the end. Pulse oximetry readings may be taken according to the algorithms described herein. Total heart rate and accelerations may be recorded over time i. At the end of time i, the time interval until resting heart rate resumes may be recorded and HRR may be calculated. The algorithm may then calculate HR, MHR, PMHR, HRV, HRR, MP and GFF.

Turning now to FIGS. 1-2, the figures illustrate the anatomy of a user's right arm, specifically, the major arteries. The arteries are depicted from both a superficial view (anatomy under the dermis and epidermis—FIG. 1) and deep view (anatomy under the dermis, epidermis and partial muscle lawyer—FIG. 2). As stated above, it is envisioned that the underside of the wrist may provided superficial vasculature from the radial 201 and/or ulnar artery 202 as well as capillary beds (not specifically labeled). A person having ordinary skill in the art understands that the blood running through major blood vessels, as opposed to capillary beds, may represent a more desirable target for the generation of pulse oximetry readings.

A major blood vessel may be a more desirable target than capillary beds for pulse oximetry measurements for a number of reasons. First, capillary beds, although readily available in most superficial target tissue segments of a user's right arm, do not channel sufficient volumes of blood in any one area to generate a useful pulse oximetry readings—readings taken from capillary beds are necessarily readings resulting from the aggregation of light reflected from numerous capillaries and non-vessel tissue alike. Therefore, the pulse oximetry reading for a particular time are generally inaccurate despite being generally precise when obtained from the capillary bed of a target tissue segment. Second, during trauma events, physiological responses by a user's body constrict capillary beds in order to direct blood flow to the vital organs (typically towards the trunk of the user) thereby rendering capillary beds only marginally useful, if at all useful, for detecting a pulse oximetry reading. Notably, however, this effect during trauma is less pronounced in the major arteries and, as such, pulse oximetry readings generated from major arteries may be useful even in trauma situations.

FIG. 1 and FIG. 2 support the conclusion that obtaining accurate and precise pulse oximetry readings from the arteries of a target tissue segment may be difficult, if not impossible, for pulse oximetry technologies currently known in the art. The deep view of FIG. 2, for example, may falsely lead one to conclude that there are various target tissue segments from which to target an artery. As stated above, the deep view illustrates the anatomy under the dermis, epidermis and partial muscle lawyer. Therefore, target tissue segments allowing for sufficient translucent tissue between the pulse oximetry sensor and the artery are minimal and must be specifically targeted.

To make matters worse, of those minimal target tissue segments, the area available from which to obtain a pulse oximetry reading is generally limited to a narrow band representing the reflecting plane of the tube-like blood vessel. Therefore, the limited area represented by the blood vessel itself inherently complicates any attempt to take a pulse oximetry reading from the user's arm, which is typically moving. As is stated above, a shift in position away from the target tissue segment during the taking of a pulse oximetry reading produces inaccurate and imprecise results for technologies presently known in the art.

FIG. 3 illustrates a high level functional block diagram of an exemplary architecture of a system 10 for continuous transdermal monitoring ("CTM"). A user proximity 195 includes a hub component 100 in the form of a portable computing device and a sensor package 125. The user proximity 195 envisions a sensor package 125 in wireless communication via link 190A with a hub component 100 that is in the vicinity of a user. For example, a user wearing a sensor package 125 and carrying a portable computing device 100, such as a Smartphone, on his person would be one example of the hub component 100 and the sensor package 125 being within the user proximity 195. Another example of the hub component 100 and the sensor package 125 being within the user proximity 195 would include the sensor package 125 being worn by an athlete on a field of play and the hub component 100 being monitored by a trainer on the sidelines.

Notably, although the FIG. 3 illustration depicts a sensor package 125 and a hub component 100 within a common user proximity 195, it will be understood that not all embodiments of a CTM system and method require a hub component 100 and a sensor package 125 to be within a user proximity. That is, it is envisioned that certain functionality in a CTM embodiment may be implemented via a remote computing device such as a fitness factor server 105. In such embodiments, the sensor package 125 may communicate with the fitness factor server 105 via a communications network 191 without need to communicate 190A with a hub device 100. In other embodiments, a sensor package 125 may communicate with either or both of the fitness factor server 105 and the hub component 100. Similarly, in some embodiments, the hub component 100 may transmit data to and/or from the fitness factor server 105 via link 190B which is implemented over communications network 191.

In the FIG. 3 illustration, the sensor package 125 is shown to include a power supply 188B for powering the sensor package 125, a communications module 116B for establishing communications with either or both of hub component 100 and fitness factor server 105 via communications network 191, a processor 110B and a memory 112B. The sensor package 125 also is shown to include sensors 159 (such as may include any combination of a pulse oximeter, a co-oximeter, a core body temperature sensor, an ambient temperature sensor, an accelerometer, a GPS transceiver, a displacement sensor, an infrared detector, an array of photodiodes, one or more light emitting diodes, etc.), monitor module 114B for monitoring the sensors 159 and fitness factor ("FF") module 101B for processing physiological and/or non-physiological readings from sensors 159 according to CTM algorithms.

Similar to the sensor package 125, the hub component 100 includes a communications module 116A for transmitting and/or receiving communications over network 191 from fitness factor server 105 and/or sensor package 125, a processor 110A, a memory 112A and an FF module 101A. The hub component 100 also is shown to include a display 132 for rendering one or more outputs to a CTM user. The fitness factor server 105 is also depicted as including an FF module 101C.

Notably, not all of the components depicted in the FIG. 3 illustration are required in all CTM embodiments. That is, it is envisioned, for example, that a certain CTM embodiment may include just a single FF module 101A in a hub component while other embodiments include FF modules 101 in each of the sensor package 125, the hub component 100, and/or the fitness factor server 105. As such, it will be understood from the FIG. 1 illustration that all of certain module, or a portion of a certain module, may or may not reside in a certain component of a CTM system.

As described above, the sensor package 125 may be worn by a user such that sensors 159 monitor certain physiological and/or non-physiological parameters associated with the user. Notably, although not shown in the FIG. 1 illustration, it is envisioned that certain sensors, such as ambient temperature sensors, may reside within hub component 100 in some embodiments. The monitor module 114 monitors the sensors 159 and forwards the collected data to the FF module 101B according to instructions dictated by the FF module 101B. For example, the FF module 101B may receive accelerometer readings from an accelerometer in sensors 159 and, based on the accelerometer readings, determine that the sensor package 125 is stable in motion. The FF module 101B may subsequently instruct the monitor module 114 to record and forward a pulse oximetry reading. As another example, the FF module 101B may receive readings indicative of a shift in the position of the sensor package 125 relative to the user and, based on the shift in position, determine that a different photodiode in the sensor package 125 should be selected for determination of a pulse oximetry reading.

The data generated by the sensors 159, collected by the monitor module 114 and managed by the FF module 101B may be stored locally in the memory 112B of the sensor package 125 and/or transmitted to the hub component 100 and/or the fitness factor server 105. Once received by the hub component 100 and/or the fitness factor server 105, the FF modules 101A, 101C may use the data to generate other CTM outputs such as a fitness factor or a pulse oximetry reading. Notably, it is envisioned that certain CTM embodiments may be comprised completely within a sensor package 125, while other CTM embodiments may utilize a very streamlined sensor package 125 including only those components needed for collecting sensed data and transmitting to other components in the system.

In certain CTM embodiments, data generated by sensors 159 and transmitted to fitness factor server 105 may be stored in a database 120 for later download and utilization. Similarly, it is envisioned that either or both of sensor package 125 and hub component 100 may include a fitness factor database 120 in their respective memories 112.

The exemplary embodiments of a hub component 100 and sensor package 125 envision remote communication, real-time software updates, extended data storage, etc. and may be leveraged in various configurations by users of system 10. Advantageously, embodiments of hub components 100 and/or sensor packages 125 configured for communication via a computer system such as the exemplary system 10 depicted in FIG. 3 may leverage communications networks 191 including, but not limited to cellular networks, PSTNs, cable networks, WiFi and the Internet for, among other things, software upgrades, content updates, database queries, data transmission, etc. Other data that may be used in connection with a hub component 100 and/or sensor package 125, and accessible via the Internet or other networked system, will occur to one of ordinary skill in the art.

The illustrated computer system 10 may comprise a fitness factor server 105 that may be coupled to a network 191 comprising any or all of a wide area network ("WAN"), a local area network ("LAN"), the Internet, or a combination of other types of networks. It will be understood that the term server 105 may refer to a single server system or multiple systems or multiple servers. The server 105 may be coupled to a fitness factor database 120, as described above. The fitness factor database 120 may store various records related to, but not limited to, historical sensor reading data, fitness factor algorithms, filters/rules algorithms, user preferences, previously calculated fitness factors, trends, etc.

When the server 105 is coupled to the network 191, the server 105 may communicate through the network 130 with various different hub components 100 and sensor packages 125 associated CTM users. Each hub component 100 and/or sensor package 125 may run or execute web browsing software or functionality to access the server 105 and its various CTM applications including FF module 101C. Any device that may access the network 191 either directly or via a tether to a complimentary device, may be a hub component 100 or sensor package 125 according to the computer system 10. The hub component 100 or sensor package 125, as well as other components within system 10 such as, but not limited to, a wireless router (not shown), may be coupled to the network 191 by various types of communication links 145. These communication links 145 may comprise wired as well as wireless links. The communication links 145 allow a hub component 100 or sensor package 125 to establish virtual links 190 with the server 105 and/or each other. While a virtual link 190B, for example, is depicted between the server 105 and the hub device 100, an actual wired or wireless link 145 may exist between the server 105 and the hub device 100. This link 145 may only be used to relay data to the FF server 105 from hub component 100 or sensor package 125, depending on embodiment, as a uni-directional communications channel. In other exemplary embodiments, the FF server 105, hub component 100 and/or sensor package 125 may establish bi-directional communications over network 191 as understood by one of ordinary skill in the art.

As shown, the hub component 100 may include a display 132, a processor 110A and a communications module 116A that may include one or more of a wired and/or wireless communication hardware and a radio transceiver 117. It is envisioned that the display 132 may comprise any type of display device such as a liquid crystal display ("LCD"), a plasma display, an organic light-emitting diode ("OLED") display, a touch activated display, a cathode ray tube ("CRT") display, a brail display, an LED bank, and a segmented display. A hub component 100 may execute, run or interface to a multimedia platform that may be part of a plug-in for an Internet web browser.

The communications module 116 may comprise wireless communication hardware such as, but not limited to, a WiFi card or NFC card for interfacing with FF module 101. Further, the communications module 116 may include a cellular radio transceiver to transmit collected physiological and/or non-physiological data as well as other information to other components, as depicted in the system 10 embodiment. One of ordinary skill in the art will recognize that a communications module 116 may include application program interfaces to processor 110.

It is envisioned that a hub component 100 and/or sensor package 125 may be configured to leverage the cellular radio transceiver of the communications module 116 to transmit data, such as physiological data by way of a secure channel using wireless link 190. Communication links 145, in general, may comprise any combination of wireless and wired links including, but not limited to, any combination of radio-frequency ("RF") links, infrared links, acoustic links, other wireless mediums, wide area networks ("WAN"), local area networks ("LAN"), the Internet, a Public Switched Telephony Network ("PSTN"), and a paging network.

An exemplary hub component 100 and/or sensor package 125 may also comprise a computer readable storage/memory component 112 for storing, whether temporarily or permanently, various data including, but not limited to, physiological readings and fitness factor calculations.

Figure 4:
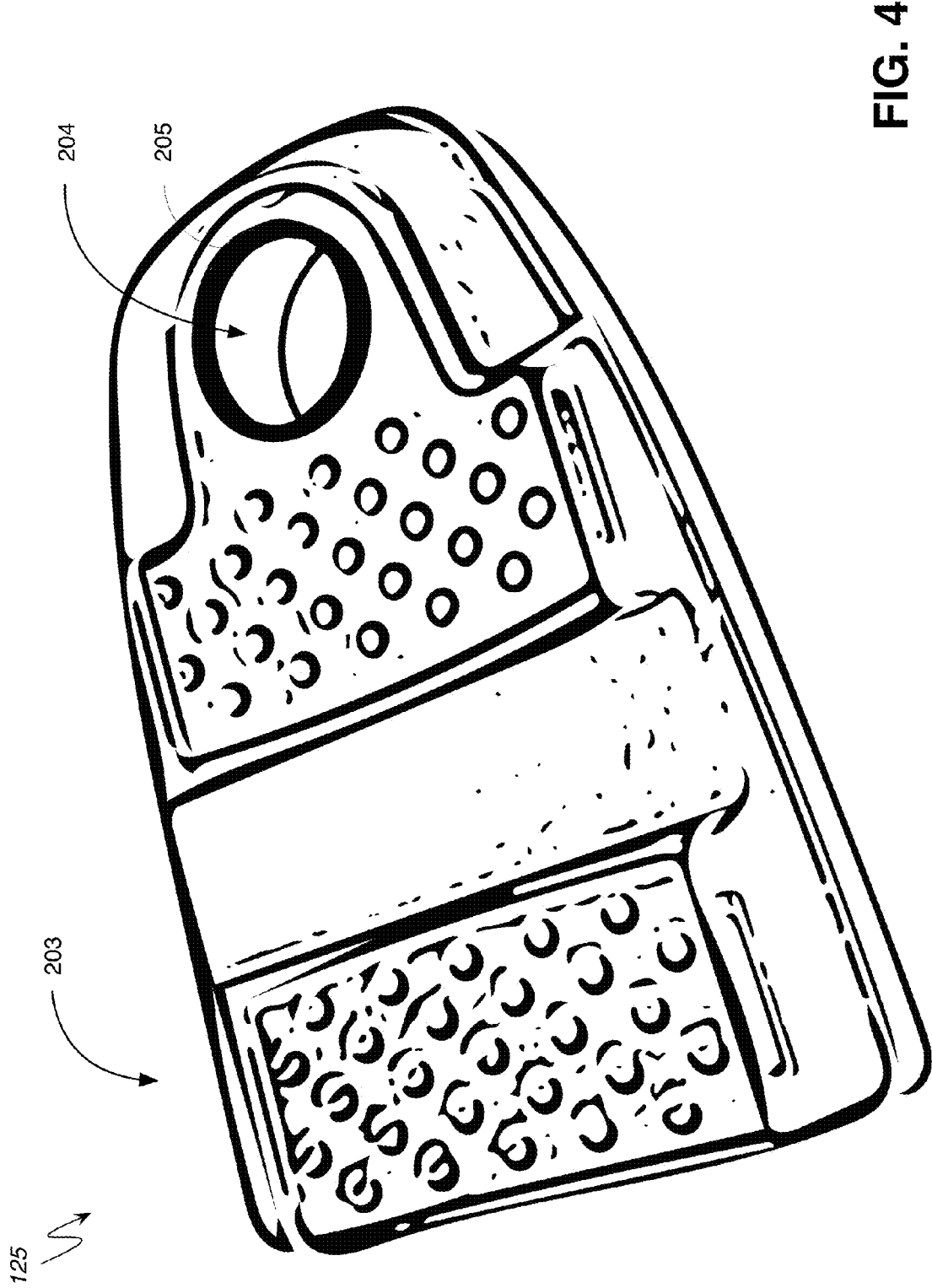
FIG. 4 is a top and side perspective view of the tissue engaging side of an exemplary embodiment of a continuous transdermal monitoring ("CTM") sensor package.

FIG. 4 is a top and side perspective view of the tissue engaging side of an exemplary embodiment of a continuous transdermal monitoring ("CTM") sensor package 125. It is envisioned that the tissue engaging side 203 of the sensor package 125 may be configured to comfortably engage with a user's tissue (not depicted), e.g., the sensor package 125 may comprise comfortable surface textures on the tissue engaging side 203 and means for detachably coupling the sensor package 125 to the user. It is envisioned that the tissue engaging side 203 of the sensor package 125 may be configured to allow sensors to align with a target tissue segment. Certain embodiments of the tissue engaging side 203 of the sensor package 125 define an aperture 204 through which a pulse oximetry sensor can direct light towards a target tissue segment and receive light reflected from the target tissue segment.

Advantageously, the aperture 204 in certain CTM embodiments may work to channel the projected and subsequently reflected light used to determine a pulse oximetry measurement. Contamination by external light sources may contribute to inaccuracies in a pulse oximetry reading, and external light contamination is common in prior art technologies when the pulse oximeter is detachably coupled to a target tissue segment that is moving. Therefore, certain embodiments of the tissue engaging side 203 of the sensor package 125 in a CTM embodiment may comprise a skirt 205 around the periphery of aperture 204 and extending towards any tissue engaging with the tissue enging side 203 of the sensor package 125. It is envisioned that the skirt 205 may be made of any flexible and/or compressible material known to one having ordinary skill in the art.

It is envisioned that that the surface of the tissue engaging side 203 of sensor package 125 along the length of the aperature 204 may be made of a material that minimizes light absorption and/or florescence, as is understood by one having ordinary skill in the art of materials. It is also envisioned that a membrane (not depicted) may extend across the aperture 204, below the skirt 205, the membrane configured to direct/focus projected light towards the target tissue segment and/or reflected light to the light detectors that form part of a pulse oximetry sensor. Certain embodiments of the membrane may be dome-like in structure and may have a plurality of layers of different materials for purposes of controlling light polarization, wavelength, intensity, etc. It is envisioned that a dome-like membrane may be concave or convex relative to the aperture 204. It is further envisioned that a membrane used in some CTM embodiments may include a raised portion substantially in its center to accommodate a height difference of a light generating component relative to an array of light detecting components.

Figure 5:
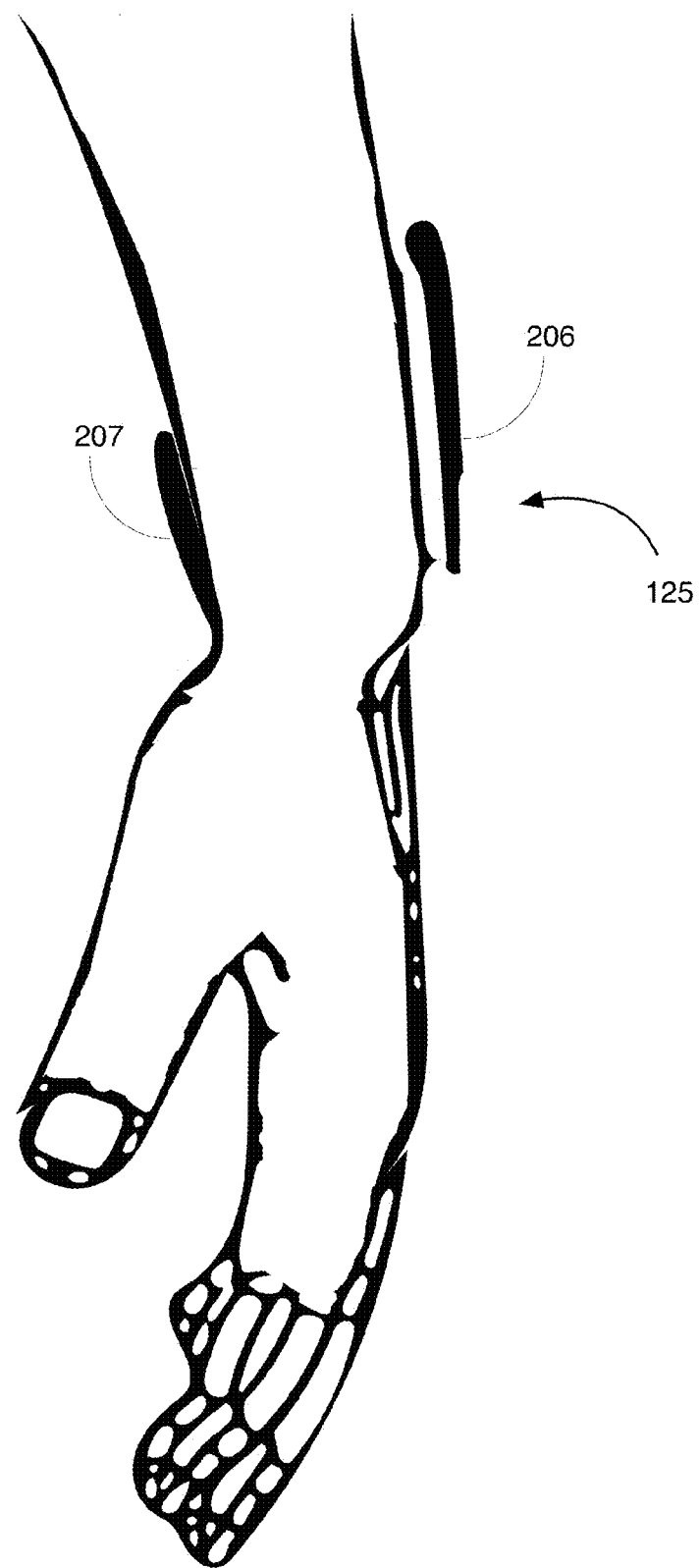
FIG. 5 is a side perspective view of a user's left arm with an exemplary continuous transdermal monitoring ("CTM") sensor package detachably coupled in one non-limiting orientation.

FIG. 5 is a side perspective view of a user's left arm with an exemplary continuous transdermal monitoring ("CTM") sensor package 125 detachably coupled in one non-limiting orientation. FIG. 5 illustrates one embodiment of a sensor package 125 without an outer housing and without any means of electrical communication. Therefore, the figure only shows the orientation of the internal circuitry of sensor package 125 relative to the targeted tissue segment; specifically, circuit board 206 and 207. It is envisioned that the internal circuitry of sensor package 125 may be held on a traditional circuit board or may be held on a printed circuit board as is understood by one having ordinary skill in the art.

Figure 6:
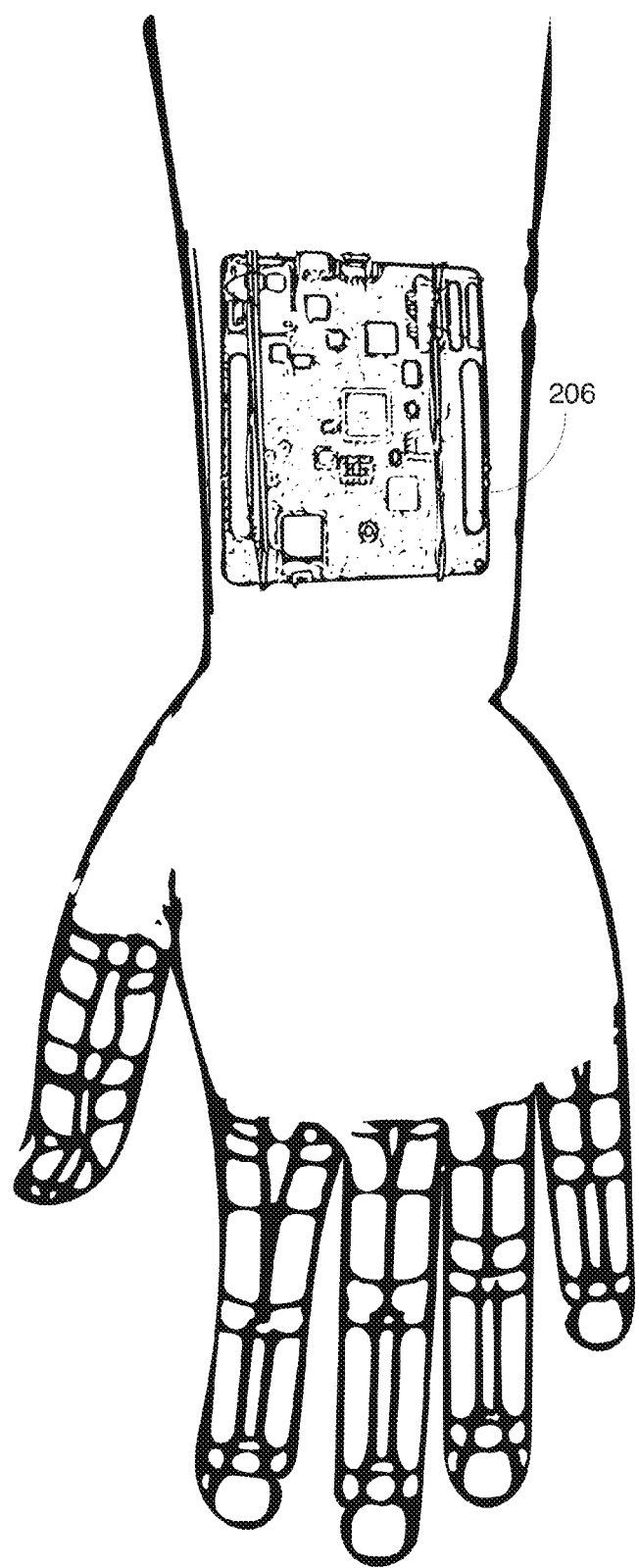
FIG. 6 is a top perspective view of a user's left arm with a circuit board of the exemplary continuous transdermal monitoring ("CTM") sensor package of FIG. 5 detachably coupled in one non-limiting orientation.

FIG. 6 is a top perspective view of a user's left arm with a circuit board of the exemplary continuous transdermal monitoring ("CTM") sensor package 125 of FIG. 5 detachably coupled in one non-limiting orientation. Certain embodiments of circuit board 206 comprise a processor 110B, a memory 101B and/or any other circuitry necessary for running a communications module 116B, a FF module 101B and a monitor module 114. Certain embodiments of circuit board 207 comprise one or more sensors 159. In particular, circuit board 207 may comprise the components for a pulse oximetry sensor (visible and labeled in FIGS. 8-9) and/or any other circuitry that may be necessary for taking a pulse oximetry reading (e.g., an accelerometer, a displacement sensor, an infrared sensor, a physiological/non-physiological parameter sensor, a transimpedance amplifier, a bandpass pass filter, a gain amplifier and an analog to digital converter) and/or any other circuitry necessary for communicating that pulse oximetry reading to the circuit board 206.

Figure 7:
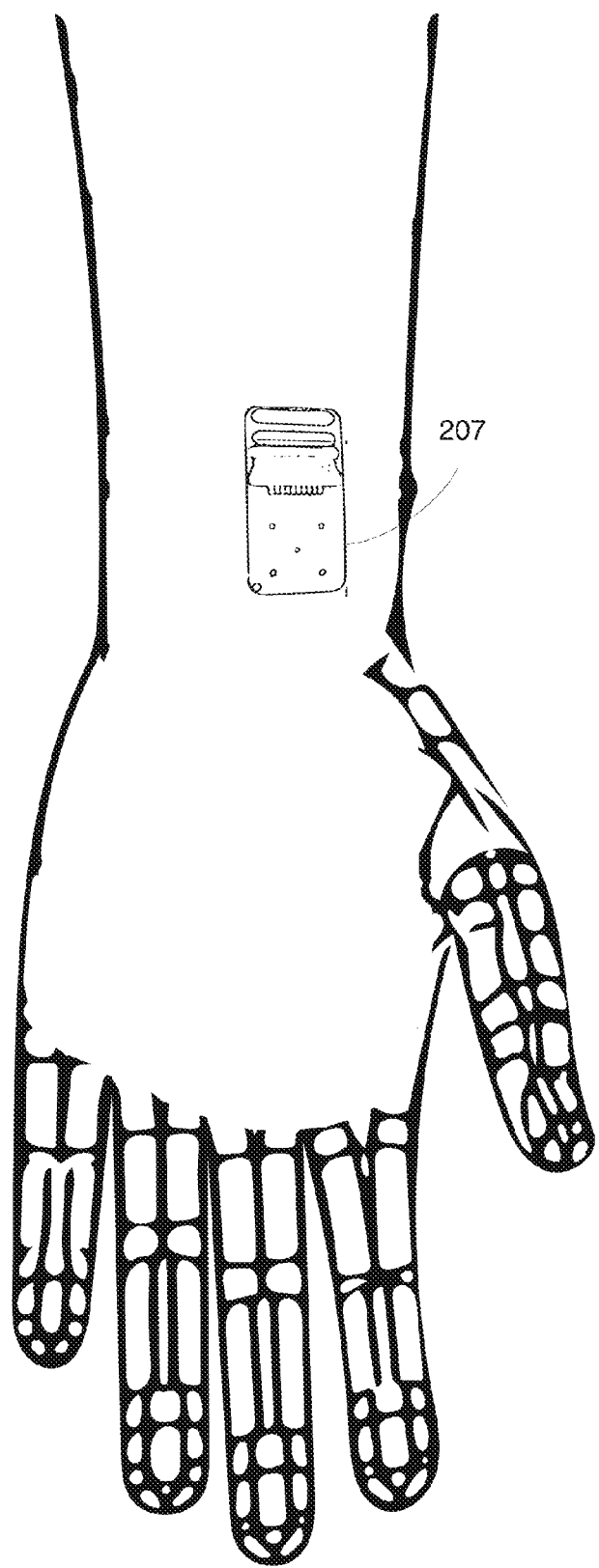
FIG. 7 is a bottom perspective view of a user's left arm with a circuit board of the exemplary continuous transdermal monitoring ("CTM") sensor package of FIG. 5 detachably coupled in one non-limiting orientation.

FIG. 7 is a bottom perspective view of a user's left arm with a circuit board of the exemplary continuous transdermal monitoring ("CTM") sensor package 125 of FIG. 5 detachably coupled in one non-limiting orientation. Although not visible in FIG. 7 (due to the circuit board 207 being oriented to position the components for a pulse oximetry sensor facing the target tissue segment), FIGS. 8-9 illustrate a schematic illustration and a top and side perspective view, respectively, of a non-limiting embodiment of the hidden side of the circuit board 207. The components for a pulse oximetry sensor held on this side of the circuit board 207 comprise a light emitter 208, an array of light detectors 209A-D, a light detector dedicated accelerometer 210 and a light detector dedicated displacement sensor 211.

It is envisioned that the light emitter 208 may comprise a red LED, an infrared LED and/or any other light emitter known to one having ordinary skill in the art. It is envisioned that the array of light detectors 209A-D may comprise a plurality of individual photodiodes, a plurality of composite photodiode sensors and/or any other light detector known to one having ordinary skill in the art. Certain embodiments of the plurality of light detectors 209A-D are structured and positioned on the circuit board 208 to function as an array of independent light detectors. An array of independent light detectors may be configured to obtain a plurality of independent pulse oximetry readings for differently defined target tissue segments. While it is possible that these defined target tissue segments may overlap, one having ordinary skill in the art understands that the pulse oximetry readings for differently defined target tissue segments are likely to vary due to differences in the underlying vasculature of the specific target tissue segment. Consequently, it is readily recognized that if a first defined target tissue segment contains more of a specifically targeted blood vessel than an adjacent slightly overlapping second defined target tissue segment, then the first target tissue segment will provide a more accurate pulse oximetry reading than the second target tissue segment.

It is envisioned that the light detector dedicated accelerometer 210 may comprise a 3-axis or 6-axis accelerometer and/or any other accelerometers known to one having ordinary skill in the art. Certain embodiments of the light detector dedicated accelerometer 210 are specifically configured to detect the acceleration of one or more light detectors of the plurality of light detectors 209A-D. Similarly, it is envisioned that the light detector dedicated displacement sensor 211 may comprise an infrared sensor, a mechanical rolling displacement sensor, a sonar sensor, a laser distance sensor and/or any other displacement sensor known to one having ordinary skill in the art. Certain embodiments of the light detector dedicated displacement sensor 211 are specifically configured to measure the displacement of one or more light detectors of the plurality of light detectors 209A-D from a specific, initial target tissue segment. If the light detector dedicated displacement sensor 211 comprises an infrared sensor, then the light detector dedicated displacement sensor 211 may be configured to visualize a blood vessel, based on reflected infrared light, within a target tissue segment. The visualization information may then be leveraged, at least in part, to measure the displacement of one or more light detectors of the plurality of light detectors 209A-D from a specific target tissue segment.

Figure 10:
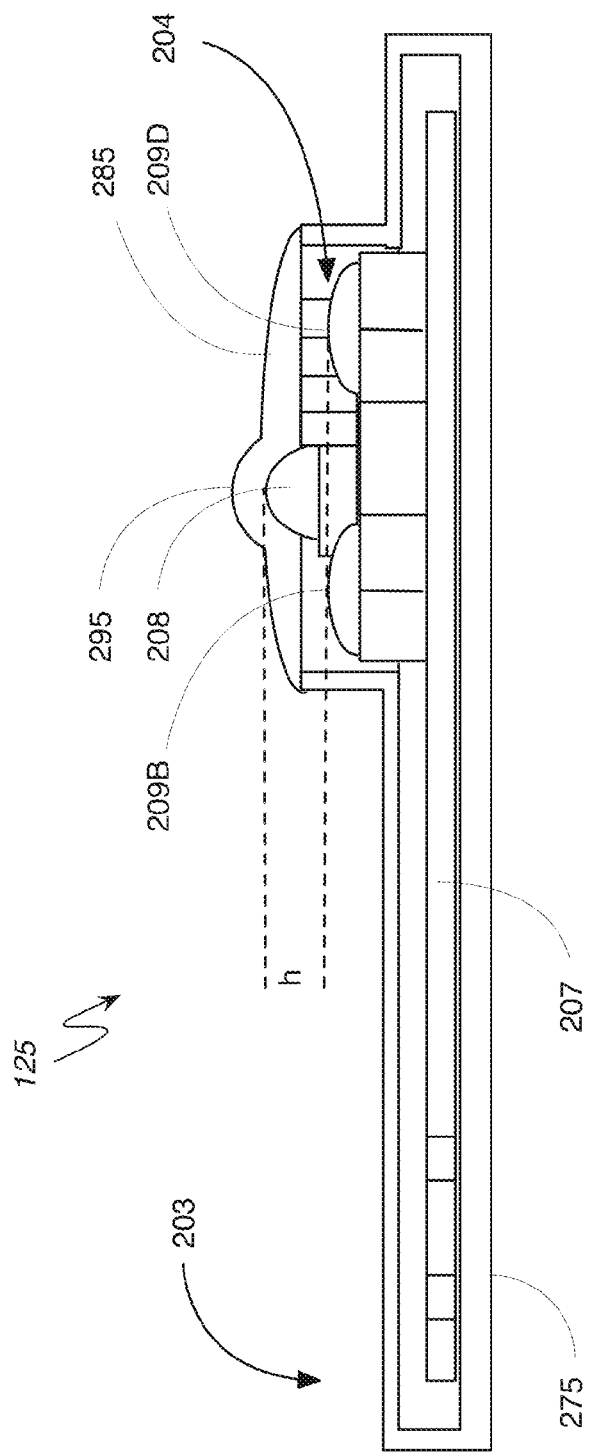
FIG. 10 is a side cross sectional view of an exemplary continuous transdermal monitoring ("CTM") sensor package.

FIG. 10 is a side cross sectional view of an exemplary continuous transdermal monitoring ("CTM") sensor package 125. FIG. 10 illustrates a simplified embodiment of the circuit board 207 within an embodiment of an outer housing 275 for this portion of the sensor package 125. Therefore, the figure only shows the orientation and positioning of the circuit board 207 relative to the outer housing 275.

As described herein, the outer housing 275 of this portion of the sensor package 125 comprises an embodiment of the tissue engaging side 203. The circuit board 207 comprises an embodiment of the light emitter 208 and an embodiment of the array of light detectors 209A-D (only 209B and 209D are visible from this cross section view). The light emitter 208 and the array of light detectors 209A-D project out from the circuit board 207 such that the tissue engaging side 203 of the outer housing 275 has a geometric configuration that conforms to the geometric configuration of the circuit board 207. The tissue engaging side 203 also defines an embodiment of the aperture 204 through which the light emitter 208 can direct light towards a target tissue segment (depicted in FIG. 11) and through which the array of light detectors 209A-D can receive light reflected from the target tissue segment (depicted in FIG. 11).

At the end of the geometric contour of the tissue engaging side 203 defining the aperture 204, the outer housing 275 additionally comprises an embodiment of a membrane 285 that extends across the aperature 204 such that the circuit board 207 and the internal space of the outer housing 275 are protected from the outside environment. It is envisioned that the membrane does not necessarily have to function as a complete barrier, instead it may function as a selective barrier and/or a permeable barrier. The membrane 285 may be translucent to any light emitted from the light emitter 208. The membrane 285 may also be substantially a convex dome with a complex shape; however, the member 285 is not limited to this specific geometric configuration.

In this particular embodiment of the sensor package 125, the complex shape of the membrane 285 includes a raised portion 295 to accommodate the light emitter 208, which extends beyond the tissue engaging side 203 when the circuit board is positioned within the outer housing 275. Not all embodiments of the sensor package 125 necessarily have a light emitter 208 that extends further from the board than the array of light detectors 209A-D; however, it may be advantageous to have a height difference, h, between the light emitter 208 and the array of light detectors 209A-D as depicted in FIG. 10.

For example, it is envisioned that having a light emitter 208 that extends beyond the tissue engaging side 203 when the circuit board is positioned within the outer housing 275 may allow for the light emitter 208 to more efficiently and effectively emit light towards/through the target tissue segment. Moreover, it is envisioned that having a light emitter 208 that extends beyond the array of light detectors 209A-D may allow for the light emitter 208 to emit light directly towards/through the target tissue segment without that light first contacting the array of light detectors 209A-D.

Figure 11:
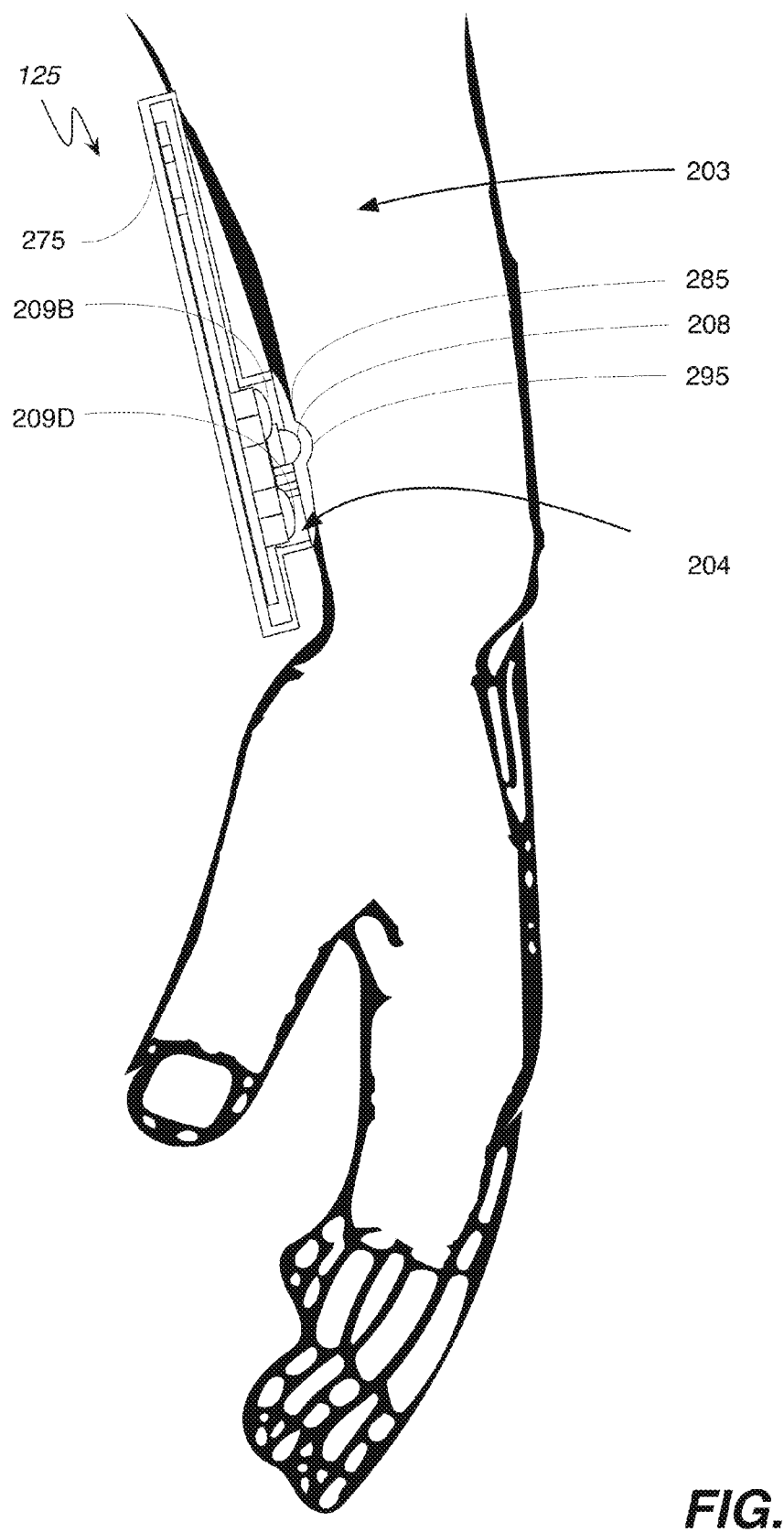
FIG. 11 is a side perspective view of a user's left arm shown with the exemplary continuous transdermal monitoring ("CTM") sensor package of FIG. 10 detachably coupled in one non-limiting orientation.

FIG. 11 is a side perspective view of a user's left arm shown with the exemplary continuous transdermal monitoring ("CTM") sensor package 125 of FIG. 10 detachably coupled in one non-limiting orientation. FIG. 11 illustrates the sensor package 125 without any means of electrical communication and without any of the other remaining portions of the sensor package 125, e.g., the circuit board 206. Therefore, the figure only shows the orientation of this portion of the sensor package 125 relative to the target tissue segment.

The tissue engaging side 203 of the outer housing 275, including the membrane 285, are comfortably engaged with a user's tissue such that the light emitter 208 and the array of light detectors 209A-D (only 209B and 209D are visible) are aligned with the target tissue segment via the aperture 204. Advantageously, the aperature 204 channels any emitted and subsequently reflected light and prevents contamination by external light sources when this portion of the sensor package 125 is engaged with the user's tissue. Moreover, the inner surface of the tissue engaging side 203 along the length of the aperature 204 may be constructed of a material that minimizes light absorption and/or florescence. The membrane 285 extends across the aperture 204 and is configured, in certain embodiments, to direct/focus light towards the target tissue segment and/or the array of light detectors 209A-D. Moreover, the membrane 285 may have, in certain embodiments, a plurality of layers of different materials for purposes of controlling light polarization, wavelength, intensity, etc.

As can be seen in the illustration, the raised portion 295 of the membrane 285 accommodates the light emitter 208, which extends beyond the tissue engaging side 203. Because the light emitter 208 extends beyond the tissue engaging side 203 and because the membrane 285 has the raised portion 295, the light emitter 208 is in close proximity with the target tissue segment when this portion of the sensor package 125 is engaged with the user's tissue. Therefore, the user's tissue will conform around the membrane 285, which is envisioned to mitigate contamination by external light source, and the raised portion 295 will extend slightly further into the user's tissue, which may allow the light emitter 208 to emit light towards/through the target tissue segment more efficiently and effectively. Furthermore, because the light emitter 208 extends beyond the array of light detectors 209A-D within the aperture 204 (as depicted in FIG. 10 with height difference h), the light emitter 208 may emit light directly towards/through the target tissue segment without that light first contacting the array of light detectors 209A-D. As a result, it is envisioned that light detected by the light detectors may be comprised almost entirely of reflected light from the target tissue segment, thereby improving accuracy of a resulting pulse oximetry reading.

Figure 12:
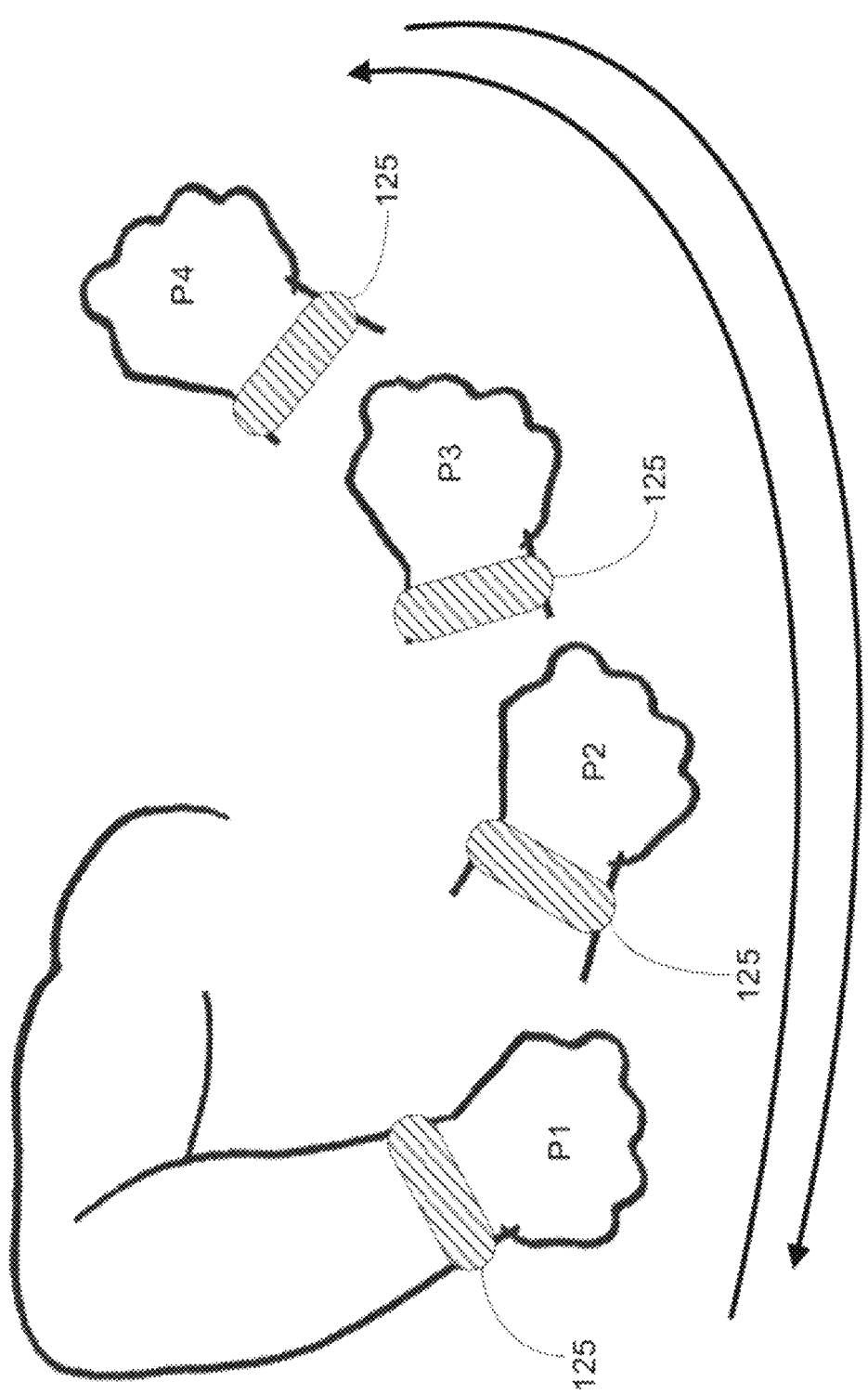
FIG. 12 is an illustration of a user's arm motion during running, the wrist of the arm depicted with a sensor package according to a continuous transdermal monitoring ("CTM") embodiment.

FIG. 12 is an illustration of a user's arm motion during running, the wrist of the arm depicted with a sensor package 125 according to a continuous transdermal monitoring ("CTM") embodiment. As can be seen in the FIG. 12 illustration, and as would be understood by one of ordinary skill in the art of running, a user's arm may translate back and forth between a forwardmost point P4 and a rearmost point P1 as the user runs. As would further be understood by one of ordinary skill in the art of running, the user may be gliding above a running surface, with neither foot in contact with the running surface, when the arm of the user is at the forwardmost and rearmost points P4 and P1, respectively. Advantageously, therefore, with no body part of the runner in contact with the running surface, and the arm of the runner at a momentarily stationary position before it reverses its direction of motion (points P1 and P4), a CTM embodiment may take a pulse oximetry reading with minimal noise attributable to motion artifact.

Figure 13:
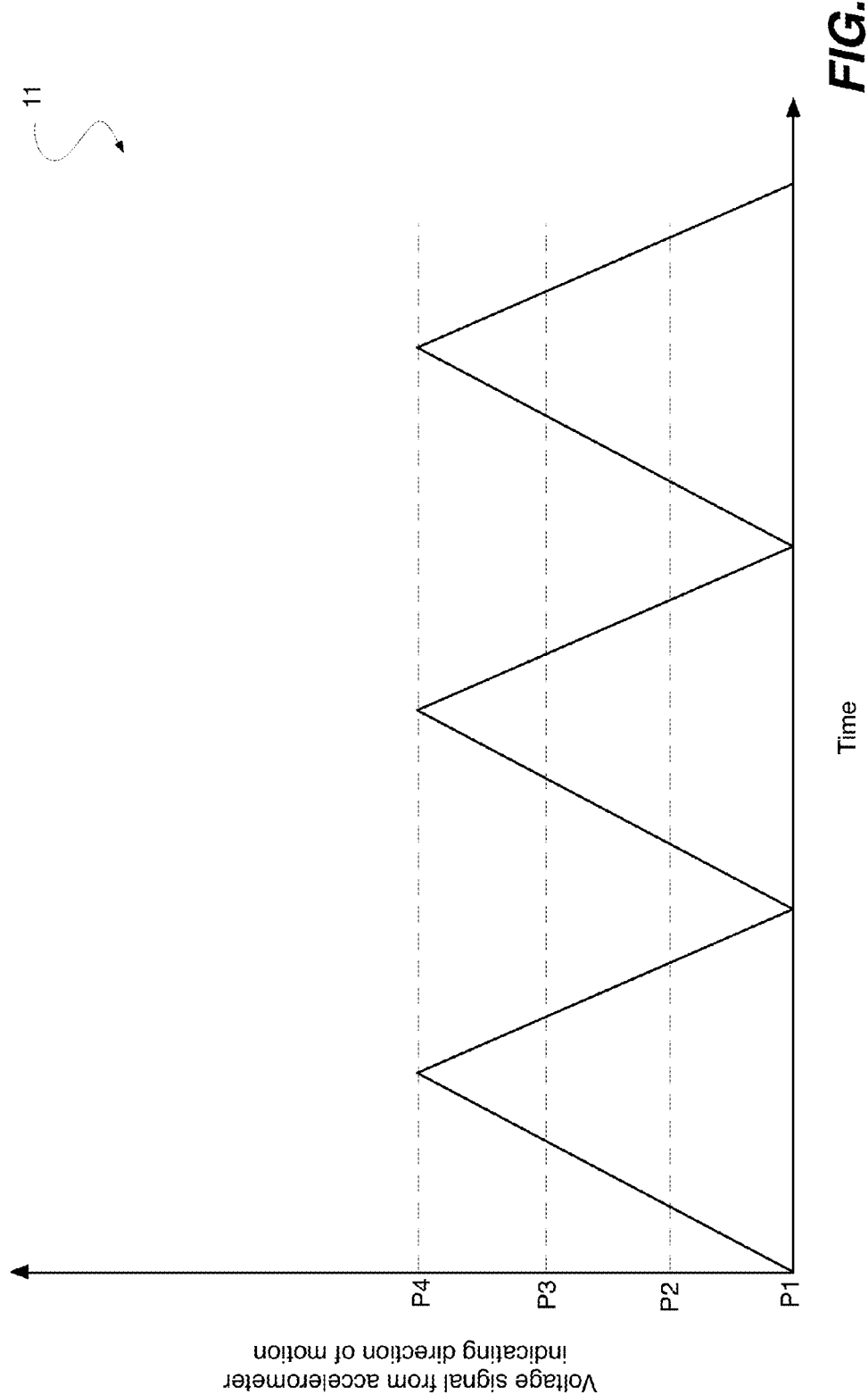
FIG. 13 is a graph illustrating an exemplary single axis output from an accelerometer sensor in the sensor package depicted in the FIG. 10 illustration.

FIG. 13 is a graph 11 illustrating an exemplary single axis output from an accelerometer sensor 159 in the sensor package 125 depicted in the FIG. 12 illustration. As the arm of the runner translates back and forth between and through positions P1 through P4, a single axis graph generated by double axis, triple axis or six axis accelerometer 159 may be generated similar to the graph 11. Notably, as the graph 11 indicates that the sensor package 125 is at either position P1 or P4, the CTM embodiment may recognize that noise attributable to a motion artifact is at a minimum. Based on such recognition the CTM embodiment may trigger a reading from a pulse oximeter, or other sensor, included in the sensors 159 of the sensor package 125.

Similarly, a CTM embodiment may track an accelerometer graph, such as exemplary graph 11 while simultaneously taking readings from a pulse oximeter and/or other sensors 159 in the sensor package 125. The entire collected data may be stored and compared to determine which of the pulse oximeter readings is associated with a time stamp that is simultaneous with, or nearly simultaneous with, either of points P1 and P4. Other methods for leveraging an accelerometer reading to optimize when to take and/or consider a reading from a different sensor 159 package are envisioned and fall within the scope of a CTM embodiment.

Figure 14:
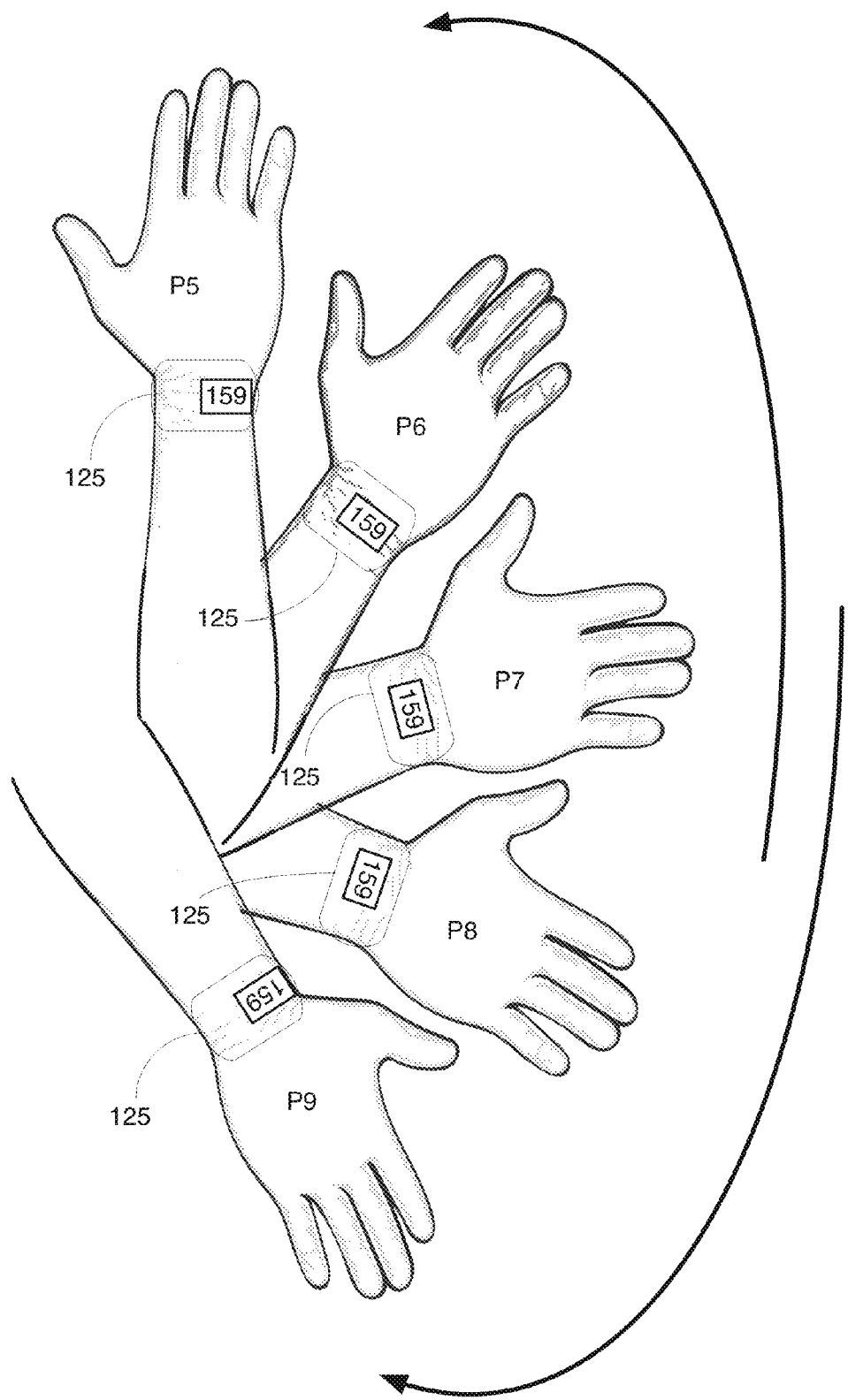
FIG. 14 is an illustration of a user's arm motion during walking, the wrist of the arm depicted with a sensor package according to a continuous transdermal monitoring ("CTM") embodiment.

FIG. 14 is an illustration of a user's arm motion during walking, the wrist of the arm depicted with a sensor package 125 according to a continuous transdermal monitoring ("CTM") embodiment. As can be seen in the FIG. 14 illustration, and as would be understood by one of ordinary skill in the art, a user's arm may translate back and forth between a upwardmost point P5 and a downwardmost point P9 as the user walks. As would further be understood by one of ordinary skill in the art, assuming a balance between comfort and security when detachably coupling the sensor package 125 to a user, a sensor 159 of the sensor package 125 is likely to experience a shift in position away from an initial target tissue segment when the user moves.

Figure 15A:
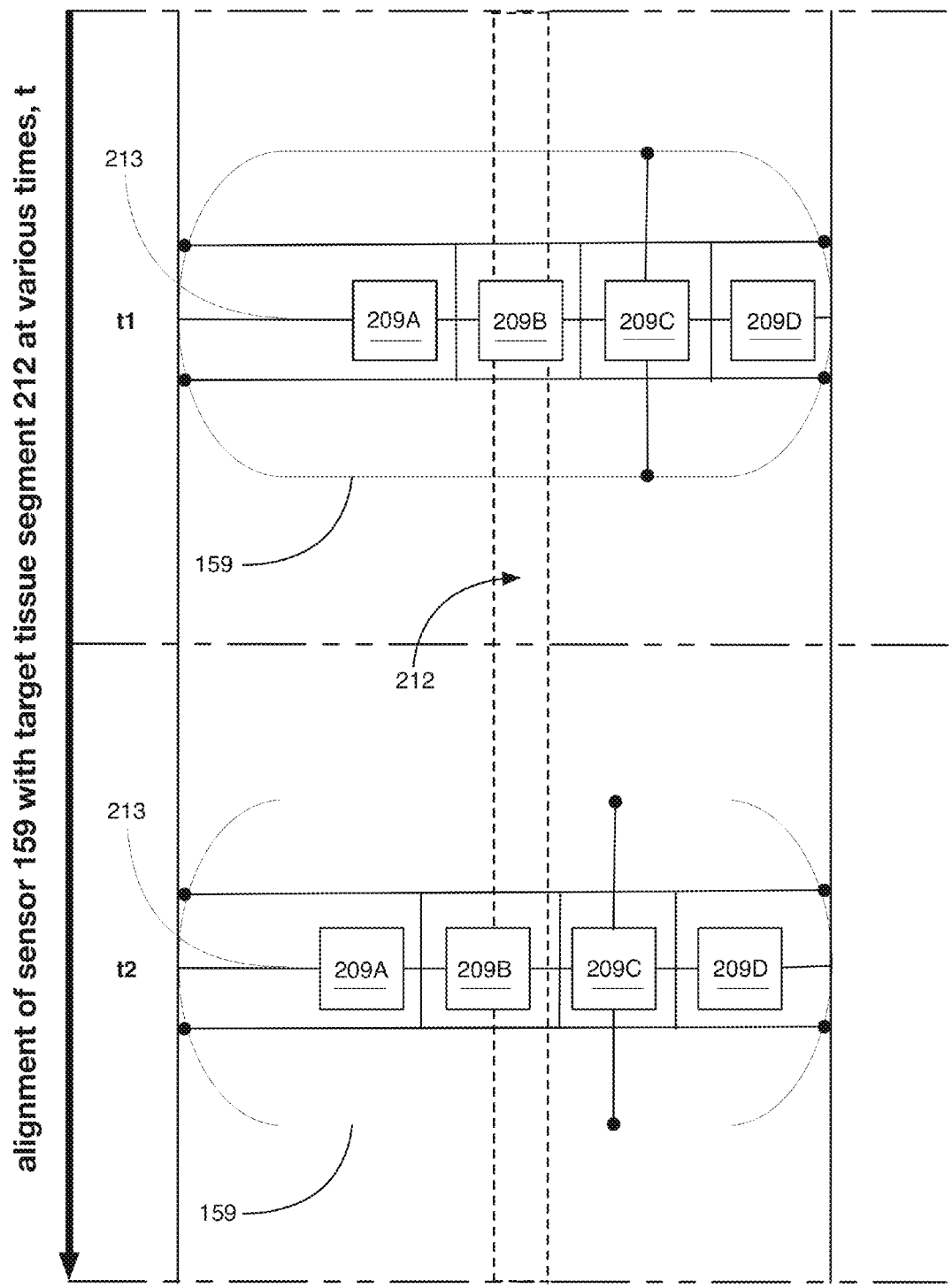
FIG. 15A is an exemplary time lapse illustration, from time t1 to t2, of an exemplary sensor of the continuous transdermal monitoring ("CTM") sensor package illustrated in FIG. 12 as the sensor shifts position relative to a target tissue segment.
Figure 15B:
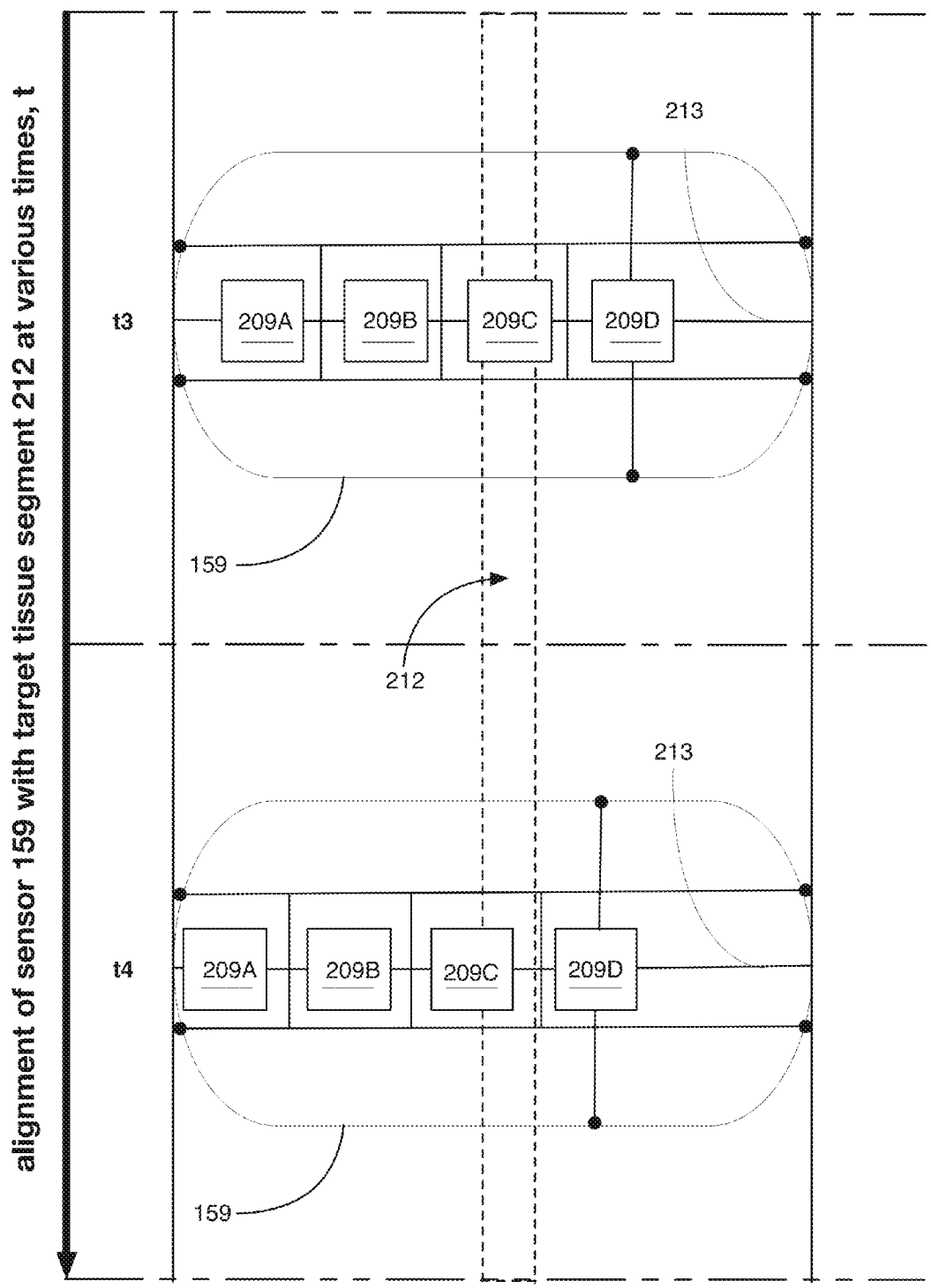
FIG. 15B is an exemplary time lapse illustration, from time t3 to t4, of an exemplary sensor of the continuous transdermal monitoring ("CTM") sensor package illustrated in FIG. 12 as the sensor shifts position relative to a target tissue segment.

FIG. 15A is an exemplary time lapse illustration, from time t1 to t2, of an exemplary sensor 159 of the continuous transdermal monitoring ("CTM") sensor package 125 illustrated in FIG. 14 as the sensor 159 shifts position relative to a target tissue segment 212. FIG. 15B is an exemplary time lapse illustration, from time t3 to t4, of the exemplary sensor 159 of the continuous transdermal monitoring ("CTM") sensor package 125 illustrated in FIG. 14 as the sensor continues to shift position relative to the target tissue segment 212. Together, FIGS. 15A-B are an exemplary time lapse illustration, from time t1 to t4, of the exemplary sensor 159 of the sensor package 125 as it shifts position relative to a target tissue segment 212 during the upwardmost point P5 and a downwardmost point P9 of FIG. 14.

Like the sensor 159 of FIGS. 8-9, the sensor 159 in the FIG. 15 illustration comprises a plurality of light detectors 209A-

D. FIGS. 15A-B also depict the means of electrical communication between the individual light detectors 209 and the other electronics of the sensor package 125; specifically, in the form of a bus 215. The sensor 159 is illustrated in a simplified and see-through form to facilitate illustration of the sensor 159's configuration and method for obtaining accurate and precise pulse oximetry readings from the target tissue segment 212, representative of a blood vessel, during a user's movement. As is stated above, the target tissue segment 212 represents a relatively narrow reflecting plane typical of a blood vessel.

At times t1 through t4, the plurality of light detectors 209A-D are structured and positioned to function as an array of independent light detectors configured to obtain a plurality of independent pulse oximetry readings for differently defined target tissue segments. At time t1, the tissue segment associated with light detector 209B (i.e., the tissue segment immediately beneath light detector 209B) is substantially aligned with the target tissue segment 212 while the tissue segments respectively associated with light detectors 209A and 209C-D are offset from target tissue segment 212 and therefore less than optimal for detecting light reflected from target tissue segment 212.

As stated above, it is possible that the defined tissue segments associated with light detectors 209A and 209C-D may overlap slightly with one another and with that of 209B; however, one having ordinary skill in the art understands that the pulse oximetry readings for these four differently defined tissue segments are likely to be different due to differences in the underlying vasculature associated with each defined tissue segment. More specifically, the pulse oximetry reading of the light detector 209B, for example, is inherently more accurate with respect to the target tissue segment 212 than the pulse oximetry reading of the other light detectors.

A person having ordinary skill in the art also understands that because the light detectors 209A and 209C are closer to the light detector 209B than the light detector 209D, the defined tissue segments associated with light detectors 209A and 209C likely have a greater overlap with the target tissue segment 212 than does the defined tissue segment associated with light detector 209D. Consequently, the pulse oximetry reading of the light detectors 209A and 209C may be more accurate with respect to the target tissue segment 212 than the pulse oximetry reading of the light detector 209D. Of course, as the sensor 159 shifts positions relative to the target tissue segment 212 during the upwardmost point P5 and a downwardmost point P9 of FIG. 14, the relative accuracies of the light detectors may change (as depicted in t2 of FIG. 15A and t3 and t4 of FIG. 15B).

Notably, the CTM embodiment may recognize the shift in position and amount of change in accuracy of the light detectors 209 with respect to the target tissue segment 212, for example, through an accelerometer and/or a displacement sensor included in the sensor package 125. Based on such recognition, the CTM embodiment may process the relative accuracy of a pulse oximetry reading coming from a specific light detector 209 in a light detector array and leverage that information for purposes of ignoring relatively inaccurate pulse oximetry readings and focusing on relatively accurate pulse oximetry readings. In another CTM embodiment, the information may be leveraged for purposes of assigning a relative weight of importance to each pulse oximetry reading from the individual light detectors 209 of the array and computing a composite pulse oximetry reading, based at least in part on the assigned relative weights of importance. Other methods for leveraging the relative accuracies of pulse oximetry readings from a light detector array are envisioned and fall within the scope of a CTM embodiment.

Returning to the FIG. 15 illustration, at time t1 light detector 209B is best positioned (relative to the other light detectors 209A, 209C and 209D) to detect light reflected from the target tissue segment 212. Consequently, a monitor module 114/FF module 101 in the given CTM embodiment may initially designate light detector 209B as the sensor from which a most accurate pulse oximetry reading may be associated. Notably, designation of light detector 209B as the primary detector for determining a pulse oximetry reading may be the result of a user physically aligning the sensor package 125 relative to target tissue segment 212. In some embodiments, however, designation of light detector 209B as the primary detector for determining a pulse oximetry reading may be the result of the monitor module 114/FF module 101 having made the determination based on a comparison of the initial readings from each detector 209 (e.g., the highest reading being indicative of the particular detector most likely aligned over the target vein 212).

Moving from time t1 to t2, shifting of the sensor package 125 relative to the target tissue segment 212, such as may occur due to user movement, has caused light detector 209B to shift from its original alignment. Notably, however, light detector 209B remains the sensor best positioned to receive reflected light from the target tissue segment 212. Consequently, the CTM embodiment may continue to designate light detector 209B as the primary detector even though its position relative to the target tissue segment 212 has shifted. At time t3, however, shifting of the sensor package 125 has caused light detector 209C to be the best aligned relative to the target tissue segment 212 and, as such, the CTM embodiment may recognize the shift and adjust the designation of the primary light detector from 209B to 209C. By doing so, the CTM embodiment may ensure that the particular light detector 209 being used to determine a pulse oximetry measurement is the best positioned detector. At time t4, the sensor package 125 has continued to shift relative to the target tissue segment 212, however, in the exemplary illustration light detector 209C remains the best positioned sensor.

Figure 16:
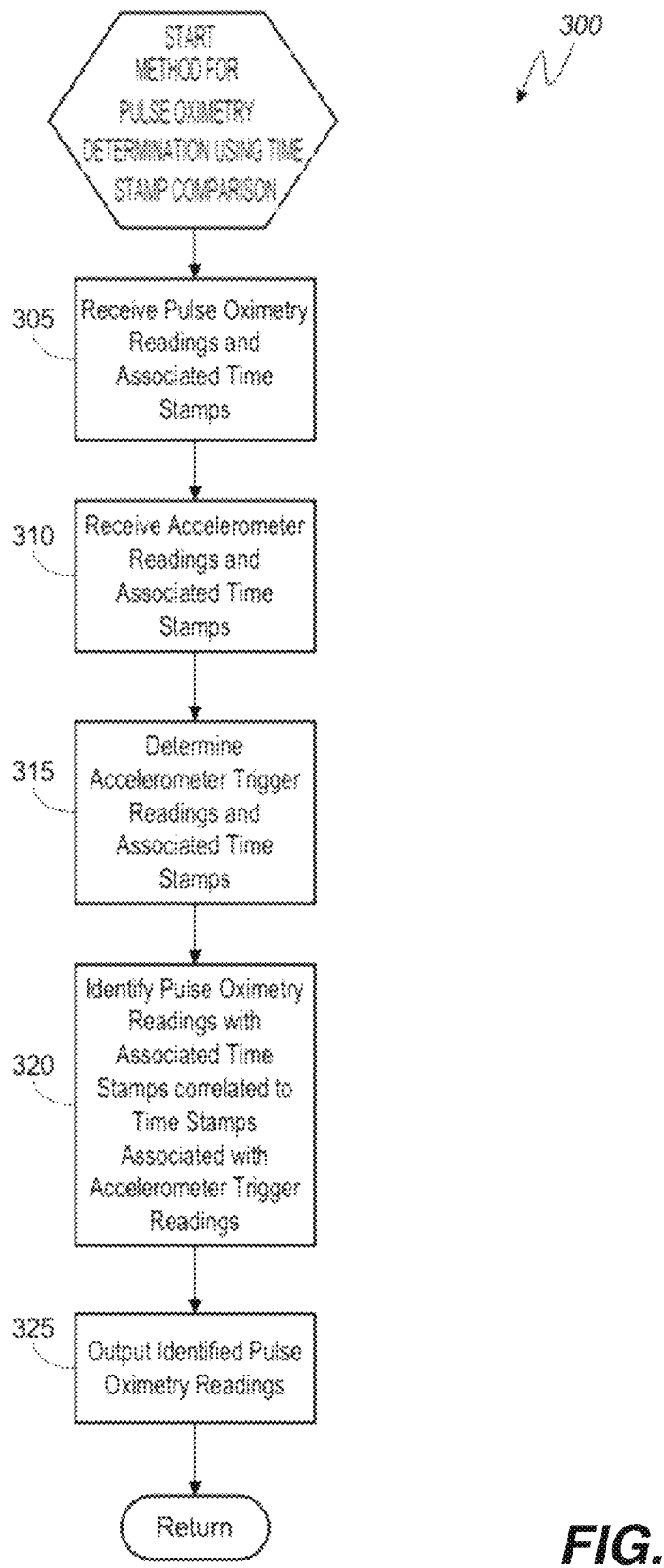
FIG. 16 is a logical flowchart illustrating a continuous transdermal monitoring ("CTM") method for pulse oximetry determination using time stamp comparison.

FIG. 16 is a logical flowchart illustrating a continuous transdermal monitoring ("CTM") method 300 for pulse oximetry determination using time stamp comparison. Beginning at block 305, pulse oximetry readings from a pulse oximeter 159 in sensor package 125 may be received continuously along with time stamps indicating when the various readings were taken. At block 310, an accelerometer 159 may be continuously monitored to generate a graph or graphs indicative of motion of the sensor package 125, such as may be correlated to the "swinging" back and forth of a runner's arm. Notably, and as would be understood by one of ordinary skill in the art of accelerometers, an accelerometer may be operable to detect motion in multiple axises which may be combined to identify points of minimal motion.

Next, at block 315 the accelerometer readings may be parsed to identify which readings are indicative of minimal motion of the sensor package. The identified readings may be considered "trigger readings" for triggering the subsequent identification of pulse oximetry readings at block 320. Notably, the time stamps associated with the accelerometer trigger readings at block 315 may be used by the CTM embodiment to identify which of the pulse oximetry readings were taken at times associated with minimal motion artifact. At block 325, the identified pulse oximetry readings may be output to the user and/or stored for later query. The method 300 returns.

Figure 17:
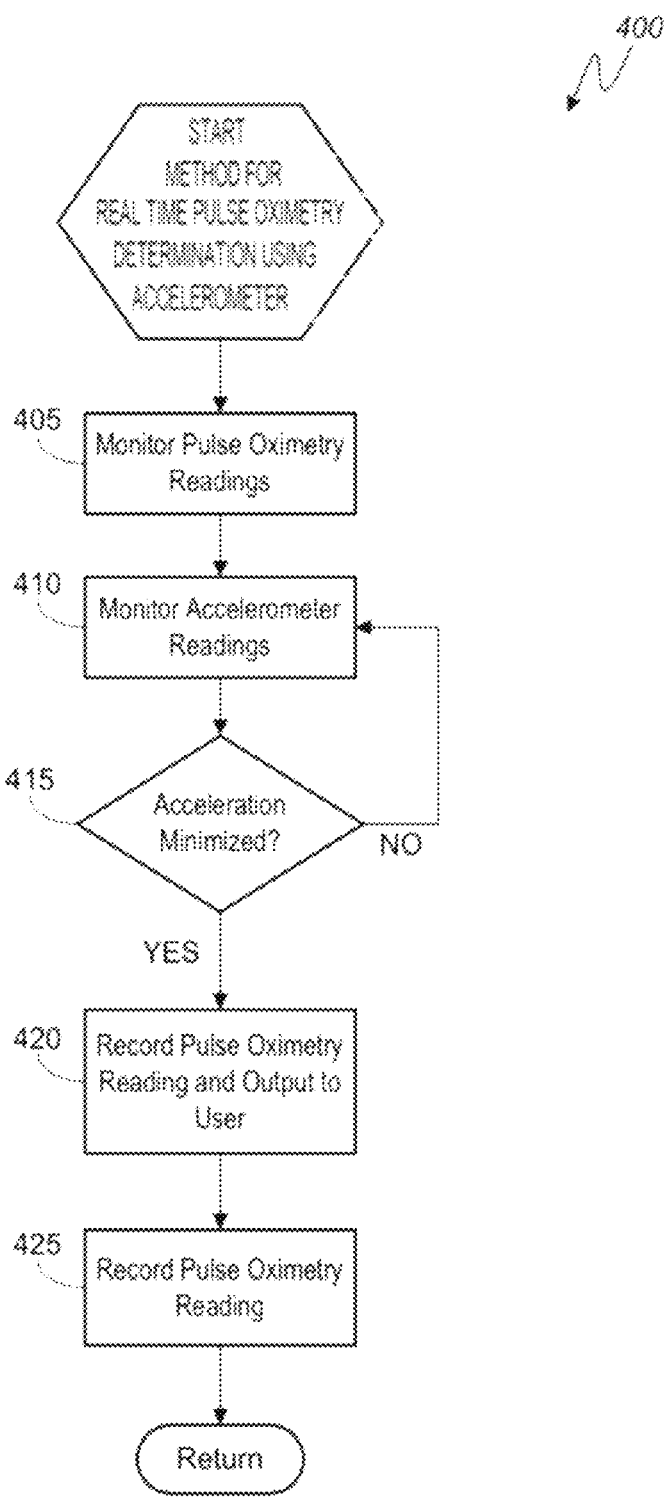
FIG. 17 is a logical flowchart illustrating a continuous transdermal monitoring ("CTM") method for near real time pulse oximetry determination based on accelerometer readings.

FIG. 17 is a logical flowchart illustrating a continuous transdermal monitoring ("CTM") method 400 for near real time pulse oximetry determination based on accelerometer readings. Beginning at block 405, pulse oximetry readings generated by a pulse oximeter sensor 159 may be monitored. Simultaneously, at block 410 an accelerometer in the sensors 159 may be monitored. Next, at decision block 415, if the monitored accelerometer readings indicate that acceleration motion is minimized, then the CTM embodiment may determine that the sensor package is momentarily stationary such that any noise attributable to motion artifact is minimized. If acceleration is not minimized, the "no" branch is followed back to block 410 and the accelerometer readings are continued to be monitored.

If, however, the accelerometer readings indicated that motion of the sensor package is minimized, then the "yes" branch is followed to block 420 and the pulse oximetry reading is recorded. At block 425, the pulse oximetry reading, which may be accurate due to the fact that it was taken at a time that motion artifact was minimized, may be output to the user and/or stored for later query. The method 400 returns.

Figure 18:
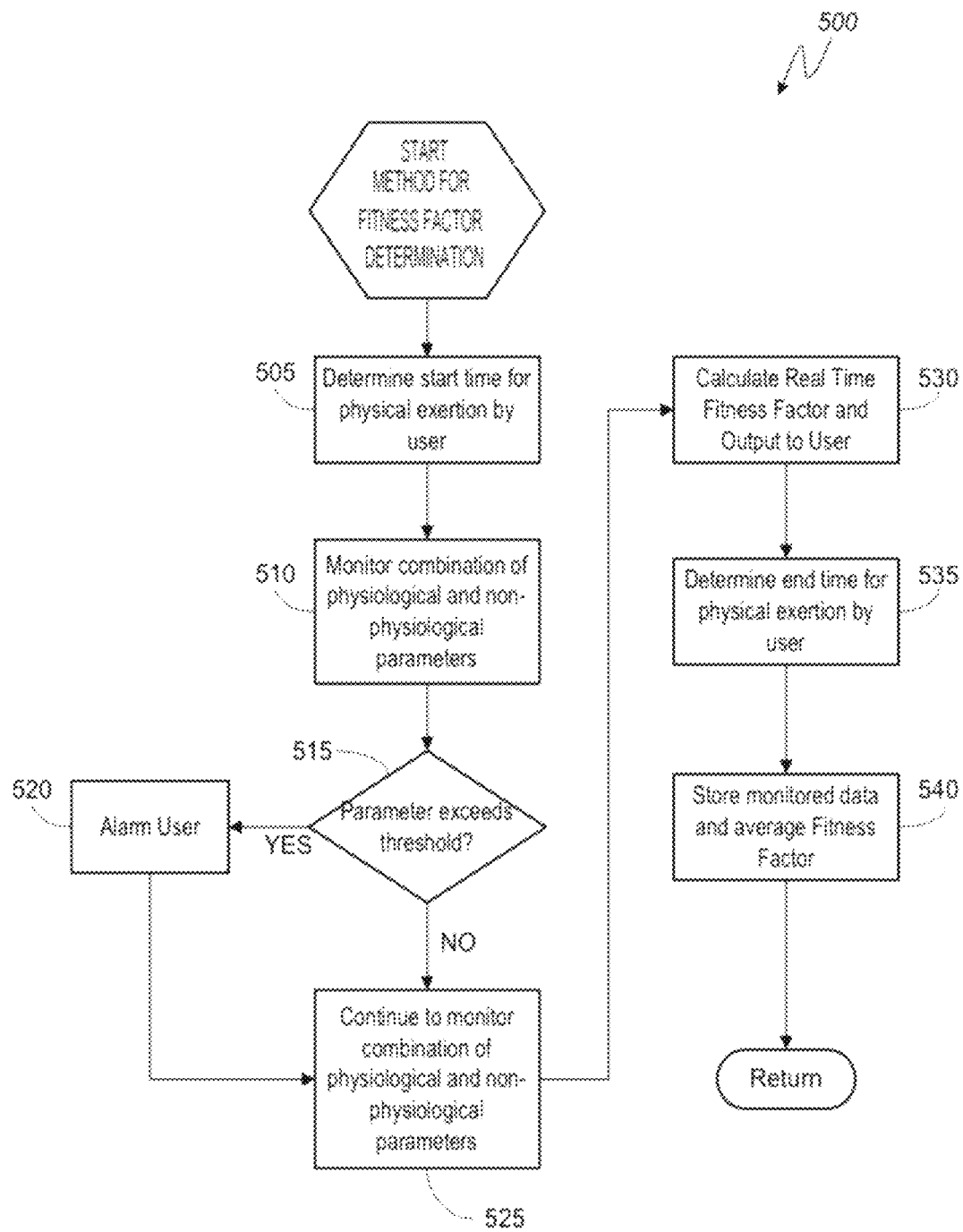
FIG. 18 is a logical flowchart illustrating a continuous transdermal monitoring ("CTM") method for generating a fitness factor output.

FIG. 18 is a logical flowchart illustrating a continuous transdermal monitoring ("CTM") method 500 for generating a fitness factor output. Beginning at block 505, a start time for a duration of physical exertion by a user may be recognized. Beginning with the start time, and throughout the duration, at block 510 one or more sensor readings indicative of physiological and/or non-physiological parameters may be monitored and tracked. At decision block 515, if any one or more of the parameters exceeds a predetermined threshold, such as for example a heart pulse rate in excess of 200 beats per minutes, then the "yes" branch may be followed to block 520 and the user alarmed. The alarm may be presented via the sensor package 125, such as through an LED display or audible tone, or through a hub component 100 in a similar manner.

Returning to the method 500, if a parameter threshold has not been exceeded, or if no parameter thresholds are set, then the "no" branch is followed to block 525 and the various parameters are continuously monitored.

Subsequently, at block 530, a real time fitness factor, generated by a FF module 101, may be output to the user. As described above, the fitness factor may be the output of a CTM algorithm that weights certain combinations of the parameters monitored and tracked by the CTM embodiment. Notably, it is envisioned that a CTM algorithm for generating a fitness factor may be customizable by the user in some embodiments. At block 535, the end time for the duration of physical exertion may be determined. Subsequently, at block 540 the various parameter data monitored during the exercise period and tracked by the CTM embodiment may be output to the user and/or stored for later query. The method 500 returns.

Figure 19:
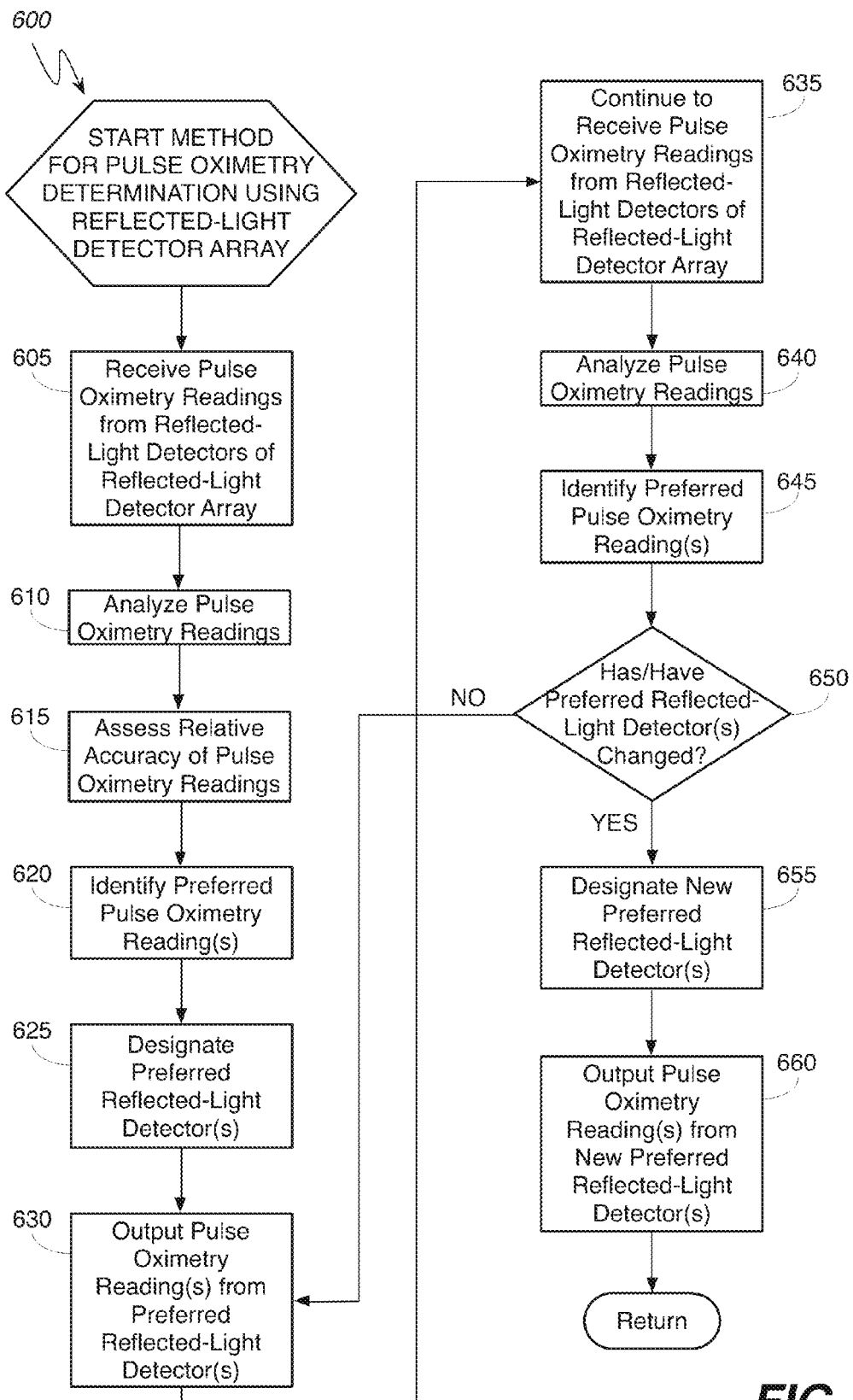
FIG. 19 is a logical flowchart illustrating a continuous transdermal monitoring ("CTM") method for pulse oximetry determination using an array of light detectors.

FIG. 19 is a logical flowchart illustrating a continuous transdermal monitoring ("CTM") method 600 for pulse oximetry determination using an array of light detectors. Beginning at block 605, separate pulse oximetry readings from the individual light detectors 209A-D of a light detector array in sensor package 125 for a target tissue segment 212 may be received. At block 610, a monitor module 114 and/or a FF module 101B may analyze the separate pulse oximetry readings from the individual light detectors 209A-D. It is envisioned that analyzing the pulse oximetry readings at block 610 may comprise running regressive and/or statistical analysis of all past pulse oximetry readings to determine if the present pulse oximetry reading is consistent with past readings. This may involve buffering and adjustments when necessary, as would be understood by one of ordinary skill in the art.

At block 615, a monitor module 114 and/or a FF module 101 may assess the relative accuracies of the seperate pulse oximetry readings with respect to the target tissue segment 212. This may involve the monitor module 114 and/or the FF module 101B receiving information about which specific light detector 209A-D is most closely aligned with the target tissue segment 212 and how the other light detectors deviate from this alignment. The monitor module 114 and/or the FF module 101 may presume that a specific light detector 209A-D is always initially aligned with the target tissue segment 212, such as may be the case when a user physically aligns the sensor package 125 with the target tissue segment 212 at initiation. In another embodiment, this may involve an alignment sensor and/or algorithm using other sensor(s) 159 data to determine which specific light detector 209A-D is best aligned with the target tissue segment 212. In another embodiment, this may involve an infrared sensor, or any other sensor known by one having ordinary skill in the art, configured to visualize the location of the target tissue segment 212. In another embodiment, the user may be able to input information into the sensor package 125 indicating which specific light detector 209A-D is best aligned with the target tissue segment 212. Other means and methods for assessing the relative accuracies of the pulse oximetry readings from the specific light detectors 209A-D of the array are envisioned and fall within the scope of a CTM embodiment.

Next, at block 620, the monitor module 114 and/or the FF module 101 may identify a preferred pulse oximetry reading(s) from the seperate pulse oximetry readings based, at least in part, on the assessed relative accuracies. One having ordinary skill in the art understands that the one or multiple pulse oximetry readings from the separate pulse oximetry readings may be identified as preferred pulse oximetry readings depending on the specific shape and configuration of the array of light detectors 209A-D. It is envisioned that the array of light detectors 209A-D is not limited to a linear side-by-side arrangement of light detectors as depicted in FIGS. 15A-B; instead different shapes and arrangements, like that shown in FIGS. 8-9 for example, are envisioned. In non-linear arrangements, multiple light detectors may be nearly identically aligned at any given point in time with the target tissue segment 212 and, therefore, would produce pulse oximetry readings having nearly identical relative accuracies.

Next, at block 625, the monitor module 114 and/or the FF module 101 may designate a preferred or primary light detector(s) from the light detectors 209A-D, based at least in part, on the identified preferred pulse oximetry reading(s). Similar to that stated above, it will be understood that the one or multiple light detectors from the light detectors 209A-D may be designated as preferred light detectors. At block 630, the pulse oximetry reading from the designated preferred light detectors is output for processing, leveraging, rendering for the user or any other third party and/or stored for later query.

Next, at block 635, further separate pulse oximetry readings from the individual light detectors 209A-D of a light detector array in sensor package 125 for a target tissue segment 212 may be received. At block 640, the monitor module 114 and/or a FF module 101B may then again analyze the newly received separate pulse oximetry readings from the individual light detectors 209A-D.

At block 645, the monitor module 114 and/or the FF module 101 may then reassess the relative accuracies of the newly received seperate pulse oximetry readings with respect to the target tissue segment 212. This may involve the monitor module 114 and/or the FF module 101B receiving information from an accelerometer, displacement sensor and/or infrared sensor about which specific light detector 209A-D have shifted in position relative to the target tissue segment 212 since actions 605-630. Determining the amount of shift may involve the monitor module 114 and/or the FF module 101 leveraging a known distance and/or position of the light detectors 209A-D with respect to one another to determine the amount and direction of the shift. In another embodiment, this may involve an alignment sensor and/or algorithm using other sensor(s) 159 data that determines which specific light detector 209A-D is best aligned with the target tissue segment 212 after the shift. In another embodiment, this may involve an infrared sensor, or any other sensor known by one having ordinary skill in the art, configured to visualize the location of the target tissue segment 212. In another embodiment, the user may be able to input information into the sensor package 125 indicating which specific light detector 209A-D is best aligned with the target tissue segment 212 after the shift. Other means and methods for assessing the relative accuracies of the pulse oximetry readings from the specific light detectors 209A-D of the array after the shift are envisioned and fall within the scope of a CTM embodiment.

Next, at block 645, the monitor module 114 and/or the FF module 101 may identify a preferred pulse oximetry reading(s) from the newly received seperate pulse oximetry readings, based at least in part, on the reassessed relative accuracies. At block 650, two deviations in the method occur if the identified preferred pulse oximetry reading(s) would lead to a change in the preferred light detector(s) from the light detectors 209A-D. If the identified preferred pulse oximetry reading(s) would not lead to a change in the preferred light detector(s) from the light detectors 209A-D, then the method reverts to block 630 and continues as described above.

If the identified preferred pulse oximetry reading(s) would lead to a change in the designated preferred light detector(s) from the light detectors 209A-D, then, at block 655, the monitor module 114 and/or the FF module 101 may redesignate a preferred light detector(s) from the light detectors 209A-D, based at least in part, on the newly identified preferred pulse oximetry reading(s). At block 660, the pulse oximetry reading from the redesignated preferred light detectors may be output for processing, leveraging, rendering for the user or any other third party and/or stored for later query.

Figure 20:
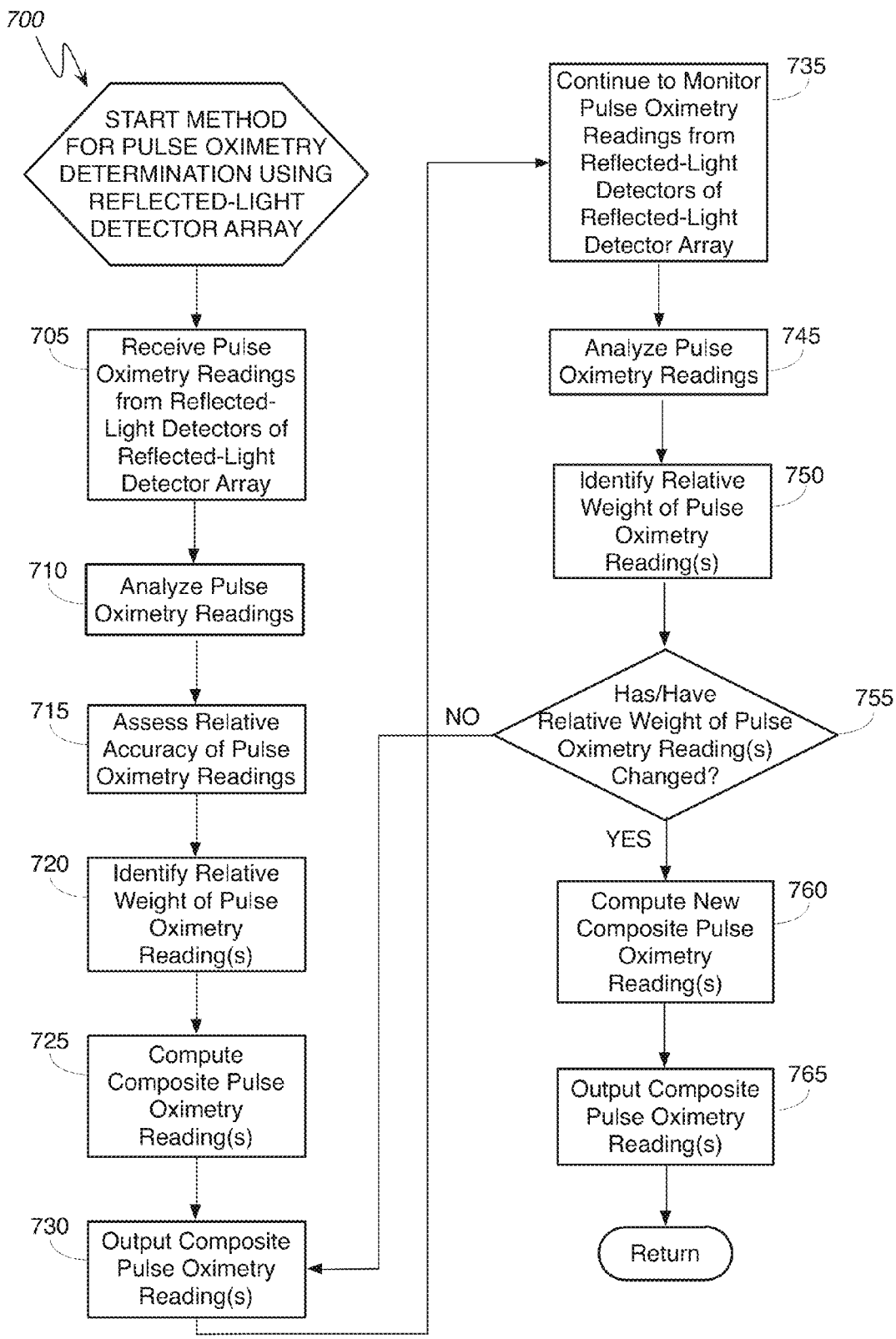
FIG. 20 is a logical flowchart illustrating a continuous transdermal monitoring ("CTM") method for pulse oximetry determination using an array of light detectors.

FIG. 20 is a logical flowchart illustrating another continuous transdermal monitoring ("CTM") method 700 for pulse oximetry determination using an array of light detectors. The method 700 is essentially identical to the method 600 described above; however, instead of identifying a preferred pulse oximetry reading(s) from the separate pulse oximetry readings based, at least in part, on the assessed relative accuracies, the method 700, at block 720, identifies a relative weight of importance assignable to each pulse oximetry reading from the light detectors 209A-D. In the exemplary method 700 embodiment, one or multiple pulse oximetry readings from the separate pulse oximetry readings may be assigned the same relative weight of importance depending on the specific shape and configuration of the array of light detectors 209A-D.

Next, instead of designating a preferred light detector(s) from the light detectors 209A-D based, at least in part, on the identified preferred pulse oximetry reading(s), the method 700, at block 725, computes a composite pulse oximetry reading(s) based, at least in part on the assigned relative weights of importance. Therefore, in this exemplary embodiment, every pulse oximetry reading no matter how inaccurate may theoretically be included in the composite pulse oximetry reading; however, it is envisioned that some relative weights of importance may be assigned a 0.00 relative weight of importance. Moreover, in certain embodiments, multiple composite pulse oximetry readings may be computed; these may be made up of various combinations of the pulse oximetry readings from the light detectors 209A-D along with their assignable relative weights of importance.

As a result of the above differences between the method 600 and the method 700, at block 756, two deviations in the method 700 occur that are different from the method 600. If the identified relative weight of importance assignable to each pulse oximetry reading from the light detectors 209A-D has not changed, then the method 700 reverts to block 730 at which the computed composite pulse oximetry reading(s) may be output for processing, leveraging, rendering for the user or any other third party and/or stored for later query. If the identified relative weight of importance assignable to each pulse oximetry reading from the light detectors 209A-D has changed, then, at block 760, the monitor module 114 and/or the FF module 101 may recompute the composite pulse oximetry reading(s) based, at least in part, on the reassigned relative weights of importance.

Figure 21:
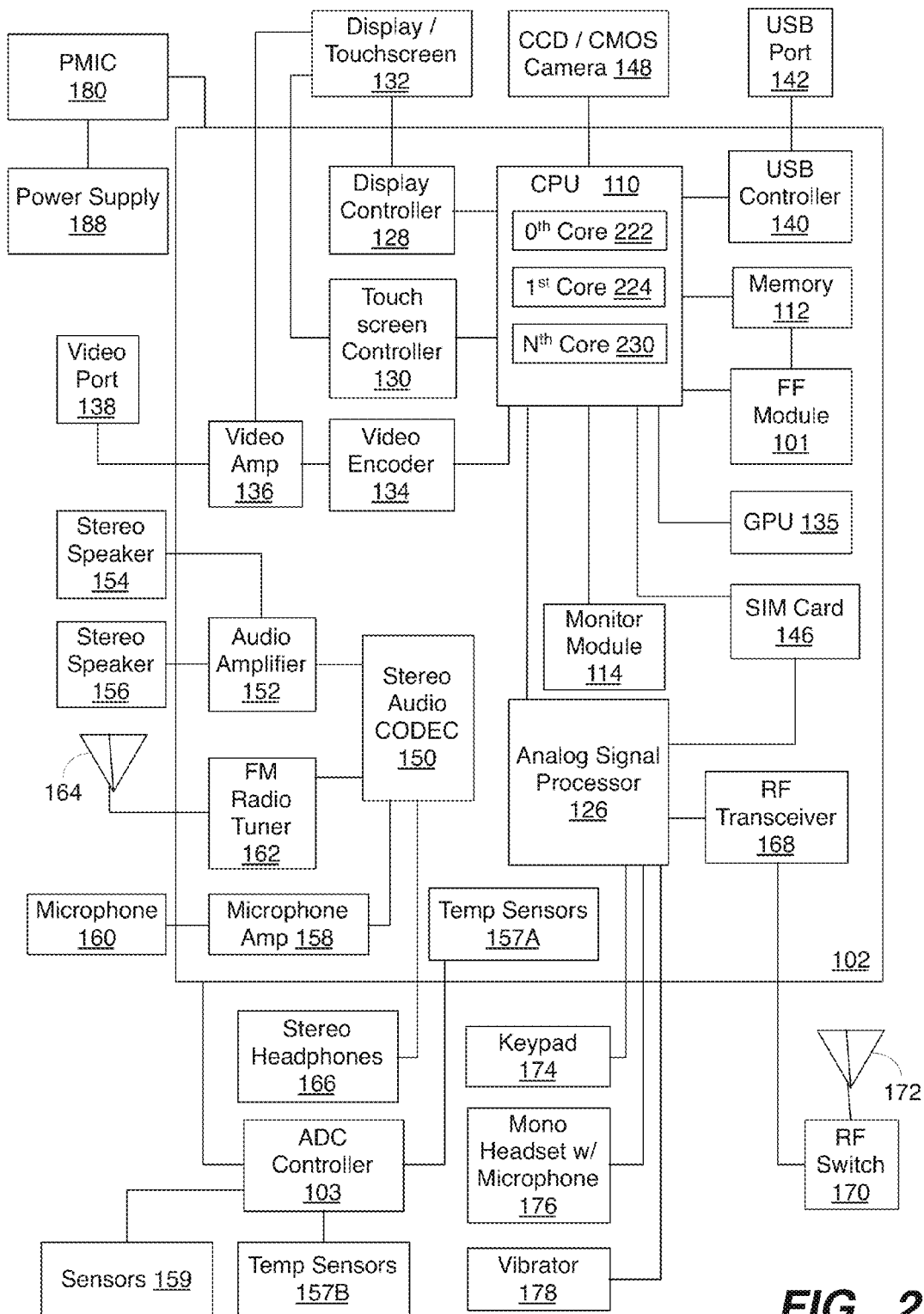
FIG. 21 is a functional block diagram illustrating an exemplary, non-limiting aspect of a portable computing device ("PCD") in the form of a wireless telephone for implementing continuous transdermal monitoring ("CTM") methods and systems.

FIG. 21 is a functional block diagram illustrating an exemplary, non-limiting aspect of a portable computing device ("PCD"), such as a hub component 100 and/or a sensor package 125, for implementing continuous transdermal monitoring ("CTM") methods and systems. The PCD may be in the form of a wireless telephone in some CTM embodiments. As shown, the PCD 100, 125 includes an on-chip system 102 that includes a multi-core central processing unit ("CPU") 110 and an analog signal processor 126 that are coupled together. The CPU 110 may comprise a zeroth core 222, a first core 224, and an Nth core 230 as understood by one of ordinary skill in the art. Further, instead of a CPU 110, a digital signal processor ("DSP") may also be employed as understood by one of ordinary skill in the art.

In general, fitness factor ("FF") module 101 may be formed from hardware and/or firmware and may be responsible for determining when and which certain sensor readings should be taken and calculating a fitness factor according to one or more fitness factor algorithms. It is envisioned that fitness factor algorithms in some CTM embodiments may be customizable by a user.

As illustrated in FIG. 21, a display controller 128 and a touch screen controller 130 are coupled to the digital signal processor 110. A touch screen display 132 external to the on-chip system 102 is coupled to the display controller 128 and the touch screen controller 130. PCD 100, 125 may further include a video encoder 134, e.g., a phase-alternating line ("PAL") encoder, a sequential couleur avec memoire ("SECAM") encoder, a national television system(s) committee ("NTSC") encoder or any other type of video encoder 134. The video encoder 134 is coupled to the multi-core CPU 110. A video amplifier 136 is coupled to the video encoder 134 and the touch screen display 132. A video port 138 is coupled to the video amplifier 136. As depicted in FIG. 21, a universal serial bus ("USB") controller 140 is coupled to the CPU 110. Also, a USB port 142 is coupled to the USB controller 140. A memory 112, which may include a PoP memory, a cache 116, a mask ROM/Boot ROM, a boot OTP memory, a DDR memory 115 may also be coupled to the CPU 110. A subscriber identity module ("SIM") card 146 may also be coupled to the CPU 110. Further, as shown in FIG. 21, a digital camera 148 may be coupled to the CPU 110. In an exemplary aspect, the digital camera 148 is a charge-coupled device ("CCD") camera or a complementary metal-oxide semiconductor ("CMOS") camera.

As further illustrated in FIG. 21, a stereo audio CODEC 150 may be coupled to the analog signal processor 126. Moreover, an audio amplifier 152 may be coupled to the stereo audio CODEC 150. In an exemplary aspect, a first stereo speaker 154 and a second stereo speaker 156 are coupled to the audio amplifier 152. FIG. 21 shows that a microphone amplifier 158 may be also coupled to the stereo audio CODEC 150. Additionally, a microphone 160 may be coupled to the microphone amplifier 158. In a particular aspect, a frequency modulation ("FM") radio tuner 162 may be coupled to the stereo audio CODEC 150. Also, an FM antenna 164 is coupled to the FM radio tuner 162. Further, stereo headphones 166 may be coupled to the stereo audio CODEC 150.

FIG. 21 further indicates that a radio frequency ("RF") transceiver 168 may be coupled to the analog signal processor 126. An RF switch 170 may be coupled to the RF transceiver 168 and an RF antenna 172. As shown in FIG. 21, a keypad 174 may be coupled to the analog signal processor 126. Also, a mono headset with a microphone 176 may be coupled to the analog signal processor 126. Further, a vibrator device 178 may be coupled to the analog signal processor 126. FIG. 21 also shows that a power supply 188, for example a battery, is coupled to the on-chip system 102 through a power management integrated circuit ("PMIC") 180. In a particular aspect, the power supply 188 includes a rechargeable DC battery or a DC power supply that is derived from an alternating current ("AC") to DC transformer that is connected to an AC power source. In another particular aspect, the power supply 188 includes a kinetically rechargeable DC battery.

The CPU 110 may also be coupled to one or more internal, on-chip thermal sensors 157A as well as one or more external, off-chip thermal sensors 157B and physiological sensors 159. The on-chip thermal sensors 157A may comprise one or more proportional to absolute temperature ("PTAT") temperature sensors that are based on vertical PNP structure and are usually dedicated to complementary metal oxide semiconductor ("CMOS") very large-scale integration ("VLSI") circuits. The off-chip thermal sensors 157B may comprise one or more thermistors. The thermal sensors 157 may produce a voltage drop that is converted to digital signals with an analog-to-digital converter ("ADC") controller (not shown). However, other types of thermal sensors 157 may be employed. The physiological sensors 159 may include, but are not limited to including, a pulse oximeter, a co-oximeter, a core body temperature sensor, a pulse rate sensor, an accelerometer, etc.

The touch screen display 132, the video port 138, the USB port 142, the camera 148, the first stereo speaker 154, the second stereo speaker 156, the microphone 160, the FM antenna 164, the stereo headphones 166, the RF switch 170, the RF antenna 172, the keypad 174, the mono headset 176, the vibrator 178, thermal sensors 157B, physiological sensors 159, the PMIC 180 and the power supply 188 are external to the on-chip system 102. It will be understood, however, that one or more of these devices depicted as external to the on-chip system 102 in the exemplary embodiment of a PCD 100, 125 in FIG. 21 may reside on chip 102 in other exemplary embodiments.

In a particular aspect, one or more of the method steps described herein may be implemented by executable instructions and parameters stored in the memory 112 or as form the FF module 101. Further, the FF module 101, the memory 112, the instructions stored therein, or a combination thereof may serve as a means for performing one or more of the method steps described herein.

Figure 22:
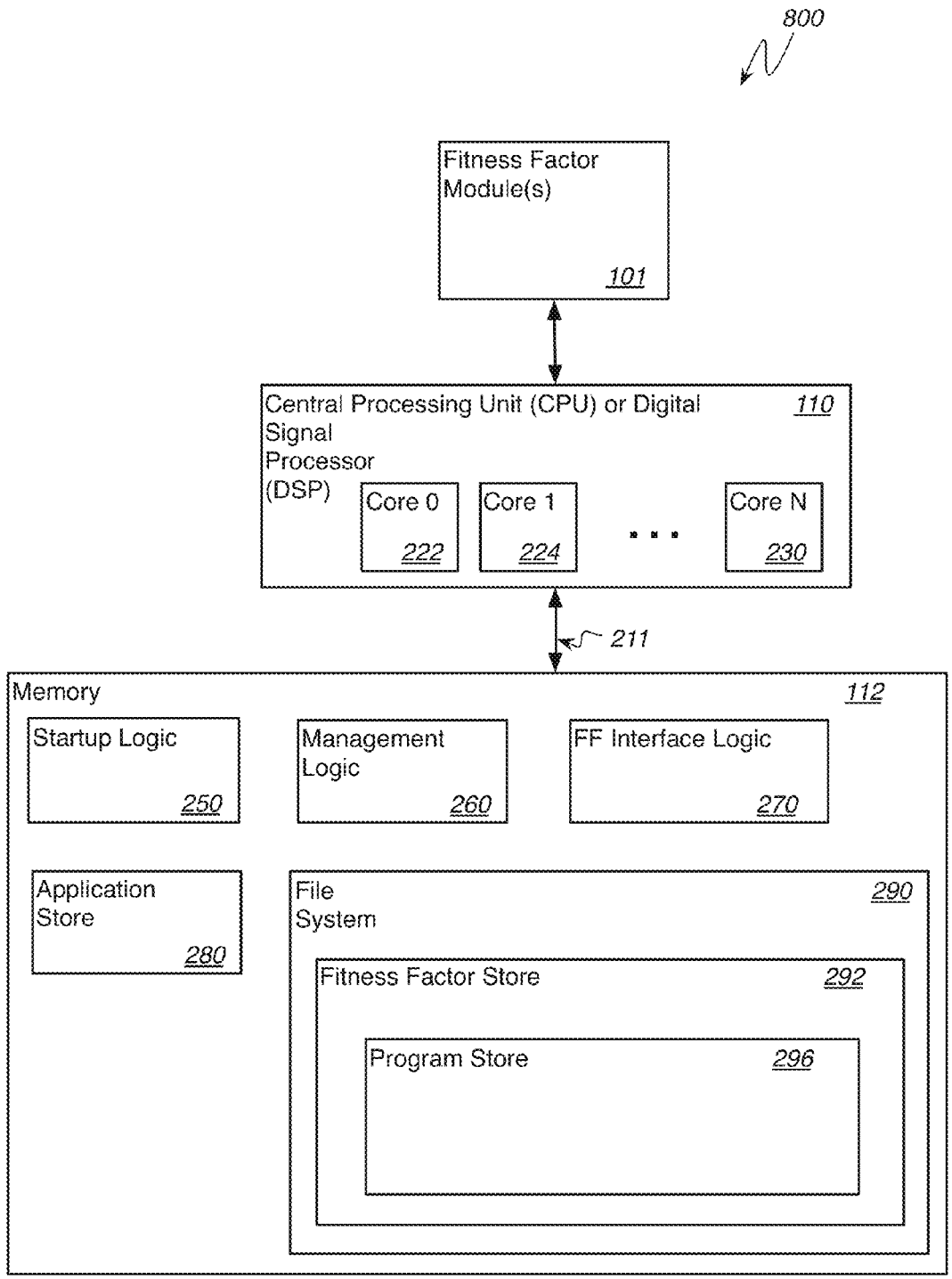
FIG. 22 is a schematic diagram illustrating an exemplary software architecture for continuous transdermal monitoring ("CTM") embodiments.

FIG. 22 is a schematic diagram illustrating an exemplary software architecture 800 for continuous transdermal monitoring ("CTM") embodiments. As illustrated in FIG. 22, the CPU or digital signal processor 110 is coupled to the memory 112 via main bus 211. The memory 112 may reside within a hub component 100, a sensor package 125 or a combination thereof. Similarly, it will be understood that the FF module 101 and the CPU 110 may reside within a hub component 100, a sensor package 125 or a combination thereof.

The CPU 110, as noted above, is a multiple-core processor having N core processors. That is, the CPU 110 includes a first core 222, a second core 224, and an $N^{th}$ core 230. As is known to one of ordinary skill in the art, each of the first core 222, the second core 224 and the $N^{th}$ core 230 are available for supporting a dedicated application or program. Alternatively, one or more applications or programs may be distributed for processing across two or more of the available cores.

The CPU 110 may receive commands from the fitness factor module(s) 101 that may comprise software and/or hardware. If embodied as software, the module(s) 101 comprise instructions that are executed by the CPU 110 that issues commands to other application programs being executed by the CPU 110 and other processors.

The first core 222, the second core 224 through to the Nth core 230 of the CPU 110 may be integrated on a single integrated circuit die, or they may be integrated or coupled on separate dies in a multiple-circuit package. Designers may couple the first core 222, the second core 224 through to the $N^{th}$ core 230 via one or more shared caches and they may implement message or instruction passing via network topologies such as bus, ring, mesh and crossbar topologies.

Bus 211 may include multiple communication paths via one or more wired or wireless connections, as is known in the art and described above in the definitions. The bus 211 may have additional elements, which are omitted for simplicity, such as controllers, buffers (caches), drivers, repeaters, and receivers, to enable communications. Further, the bus 211 may include address, control, and/or data connections to enable appropriate communications among the aforementioned components.

When the logic used by the PCD 100, 125 is implemented in software, as is shown in FIG. 22, it should be noted that one or more of startup logic 250, management logic 260, FF interface logic 270, applications in application store 280 and portions of the file system 290 may be stored on any computer-readable medium for use by, or in connection with, any computer-related system or method. In the context of this document, a computer-readable medium is an electronic, magnetic, optical, or other physical device or means that can contain or store a computer program and data for use by or in connection with a computer-related system or method. The various logic elements and data stores may be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer-readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random-access memory (RAM) (electronic), a read-only memory (ROM) (electronic), an erasable programmable read-only memory (EPROM, EEPROM, or Flash memory)

(electronic), an optical fiber (optical), Flash, and a portable compact disc read-only memory (CDROM) (optical). Note that the computer-readable medium could even be paper or another suitable medium upon which the program is printed, as the program can be electronically captured, for instance via optical scanning of the paper or other medium, then compiled, interpreted or otherwise processed in a suitable manner if necessary, and then stored in a computer memory.

In an alternative embodiment, where one or more of the startup logic 250, management logic 260 and perhaps the FF interface logic 270 are implemented in hardware, the various logic may be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The memory 112 is a non-volatile data storage device such as a flash memory or a solid-state memory device. Although depicted as a single device, the memory 112 may be a distributed memory device with separate data stores coupled to the digital signal processor 110 (or additional processor cores).

The startup logic 250 includes one or more executable instructions for selectively identifying, loading, and executing a select program for identifying accurate physiological sensor readings and/or generating a fitness factor. The startup logic 250 may identify, load and execute a select FF program. An exemplary select program may be found in the program store 296 of the embedded file system 290. The exemplary select program, when executed by one or more of the core processors in the CPU 110 may operate in accordance with one or more signals provided by the FF module 101 to identify accurate physiological sensor readings and/or generate a fitness factor.

The management logic 260 includes one or more executable instructions for terminating a CTM program on one or more of the respective processor cores, as well as selectively identifying, loading, and executing a more suitable replacement program. The management logic 260 is arranged to perform these functions at run time or while the PCD 100 is powered and in use by an operator of the device. A replacement program, which may be customized by a user in some CTM embodiments, may be found in the program store 296 of the embedded file system 290.

The interface logic 270 includes one or more executable instructions for presenting, managing and interacting with external inputs to observe, configure, or otherwise update information stored in the embedded file system 290. In one embodiment, the interface logic 270 may operate in conjunction with manufacturer inputs received via the USB port 142. These inputs may include one or more programs to be deleted from or added to the program store 296. Alternatively, the inputs may include edits or changes to one or more of the programs in the program store 296. Moreover, the inputs may identify one or more changes to, or entire replacements of one or both of the startup logic 250 and the management logic 260. By way of example, the inputs may include a change to the weight of parameters used to generate a customized fitness factor.

The interface logic 270 enables a manufacturer to controllably configure and adjust an end user's experience under defined operating conditions on the PCD 100. When the memory 112 is a flash memory, one or more of the startup logic 250, the management logic 260, the interface logic 270, the application programs in the application store 280 or information in the embedded file system 290 may be edited, replaced, or otherwise modified. In some embodiments, the interface logic 270 may permit an end user or operator of the PCD 100, 125 to search, locate, modify or replace the startup logic 250, the management logic 260, applications in the application store 280 and information in the embedded file system 290. The operator may use the resulting interface to make changes that will be implemented upon the next startup of the PCD 100, 125. Alternatively, the operator may use the resulting interface to make changes that are implemented during run time.

The embedded file system 290 includes a hierarchically arranged fitness factor store 292. In this regard, the file system 290 may include a reserved section of its total file system capacity for the storage of information for the configuration and management of the various fitness factor and/or CTM algorithms used by the PCD 100, 125.

Certain steps in the processes or process flows described in this specification naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Additionally, one of ordinary skill in programming is able to write computer code or identify appropriate hardware and/or circuits to implement the disclosed invention without difficulty based on the flow charts and associated description in this specification, for example. Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the drawings, which may illustrate various process flows.

In one or more exemplary aspects, the functions described may be implemented in hardware, software, firmware, or any combination thereof. If implemented in software, the functions may be stored on or transmitted as one or more instructions or code on a computer-readable medium. Computer-readable media include both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Therefore, although selected aspects have been illustrated and described in detail, it will be understood that various substitutions and alterations may be made therein without departing from the spirit and scope of the present invention, as defined by the following claims.

What is claimed is:

1. A system for continuous transdermal monitoring of a target tissue segment, the system comprising a sensor package comprising:

a pulse oximetry sensor comprising a plurality of light detectors arranged as an array, each of the plurality of light detectors configured to:
  detect a light reflected by the target tissue segment; and
  transmit a pulse oximetry reading of the target tissue segment, the pulse oximetry reading based, at least in part, on the light reflected by the target tissue segment;
a shift sensor configured to detect movement related information about the plurality of light detectors;
wherein the sensor package is configured to:
  designate, as a preferred light detector, a first light detector from the plurality of light detectors;
  output a pulse oximetry reading from the first light detector, based on the first light detector being designated as the preferred light detector;
  determine, based on the movement related information about detected by the shift sensor, that a second light detector from the plurality of light detectors is better positioned, relative to the target tissue segment, than the first light detector;
  designate, as the preferred light detector, the second light detector from the plurality of light detectors; and
  output a pulse oximetry reading from the second light detector, based on the second light detector being designated as the preferred light detector.

2. The system of claim 1, wherein the pulse oximetry sensor comprises a light source configured to emit light towards the target tissue segment.

3. The system of claim 1, wherein the shift sensor comprises an accelerometer.

4. The system of claim 3, wherein the accelerometer is one of the group consisting of a 3-axis accelerometer and a 6-axis accelerometer.

5. The system of claim 1, wherein the shift sensor is a displacement sensor configured to measure distance of each of the plurality of light detectors from the target tissue segment.

6. The system of claim 5, wherein the displacement sensor comprises an infrared sensor configured to visualize the location of a target blood vessel of the target tissue segment.

7. A method of continuous transdermal monitoring of a target tissue segment, the method comprising:
  designating, as a preferred light detector within a pulse oximetry sensor, a first light detector from a plurality of light detectors arranged as an array, each of the plurality of light detectors configured to detect a light reflected by the target tissue segment and transmit a pulse oximetry reading of the target tissue segment, the pulse oximetry reading based, at least in part, on the light reflected by the target tissue segment;
  outputting avulse oximetry reading from the first light detector, based on the first light detector being designated as the preferred light detector;
  determining, based on movement related information detected by a shift sensor configured to detect movement related information of the plurality of light detectors, that a second light detector from the plurality of light detectors is better positioned, relative to the target tissue segment, than the first light detector;
  designating, as the preferred light detector, the second light detector from the plurality light detectors; and
  outputting a pulse oximetry reading from the second light detector, based on the second light detector being designated as the preferred light detector.

8. The method of claim 7, wherein the pulse oximetry sensor comprises a light source configured to emit light towards the target tissue segment.

9. The method of claim 7, wherein the shift sensor comprises an accelerometer.

10. The method of claim 7, wherein the shift sensor is a displacement sensor configured to measure distance of each of the plurality of light detectors from the target tissue segment.

11. The method of claim 10, wherein the displacement sensor comprises an infrared sensor configured to visualize the location of a target blood vessel of the target tissue segment.

12. A computer program product comprising a computer usable device having a computer readable program code embodied therein, the computer readable program code adapted to be executed to implement a method for continuous transdermal monitoring, the method comprising:
  designating, as a preferred light detector within a pulse oximetry sensor, a first light detector from a plurality of light detectors arranged as an array, each of the plurality of light detectors configured to detect a light reflected by the target tissue segment and transmit a pulse oximetry reading of the target tissue segment, the pulse oximetry reading based, at least in part, on the light reflected by the target tissue segment;
  outputting avulse oximetry reading from the first light detector, based on the first light detector being designated as the preferred light detector;
  determining, based on movement related information detected by a shift sensor configured to detect movement related information of the plurality of light detectors, that a second light detector from the plurality of light detectors is better positioned, relative to the target tissue segment, than the first light detector;
  designating, as the preferred light detector, the second light detector from the plurality of light detectors; and
  outputting a pulse oximetry reading from the second light detector, based on the second light detector being designated as the preferred light detector.

13. The computer program product of claim 12, wherein the pulse oximetry sensor comprises a light source configured to emit light towards a target tissue segment.

14. The computer program product of claim 12, wherein the shift sensor comprises an accelerometer.

15. The computer program product of claim 12, wherein the shift sensor is a displacement sensor configured to measure distance of each of the plurality of light detectors from the target tissue segment.

* * * * *